(12) United States Patent
Gunderson et al.

(10) Patent No.: US 10,668,277 B2
(45) Date of Patent: Jun. 2, 2020

(54) DETECTING VENTRICULAR LEAD DISLODGEMENT

(71) Applicant: Medtronic, Inc., Minneapolis, MN (US)

(72) Inventors: Bruce D. Gunderson, Plymouth, MN (US); Charles D. Swerdlow, Los Angeles, CA (US)

(73) Assignee: Medtronic, Inc., Minneapolis, MN (US)

( * ) Notice: Subject to any disclaimer, the term of this patent is extended or adjusted under 35 U.S.C. 154(b) by 198 days.

(21) Appl. No.: 15/836,283

(22) Filed: Dec. 8, 2017

(65) Prior Publication Data

US 2018/0161572 A1    Jun. 14, 2018

Related U.S. Application Data

(60) Provisional application No. 62/432,504, filed on Dec. 9, 2016.

(51) Int. Cl.

| A61N 1/08 | (2006.01) |
|---|---|
| A61B 5/042 | (2006.01) |
| A61N 1/39 | (2006.01) |
| A61B 5/046 | (2006.01) |
| A61N 1/37 | (2006.01) |

(Continued)

(52) U.S. Cl.
CPC ............... *A61N 1/08* (2013.01); *A61B 5/042* (2013.01); *A61B 5/046* (2013.01); *A61N 1/056* (2013.01); *A61N 1/3702* (2013.01); *A61N 1/3706* (2013.01); *A61N 1/37258* (2013.01); *A61N 1/3925* (2013.01); *G16H 40/63* (2018.01); *A61N 1/3987* (2013.01); *A61N 2001/083* (2013.01)

(58) Field of Classification Search
None
See application file for complete search history.

(56) References Cited

U.S. PATENT DOCUMENTS

| 5,405,363 A | 4/1995 | Kroll et al. |
|---|---|---|
| 5,545,186 A | 8/1996 | Olson et al. |

(Continued)

OTHER PUBLICATIONS

Kelvin Chua MBBS, et al., "Defibrillation lead dislodgement: Spectrum of clinical presentations," Heart Rhythm, 14: C-PO05-48, S348, May 10-13, 2017, 3 pp. [Abstract Only].

(Continued)

*Primary Examiner* — Ankit D Tejani

(57) ABSTRACT

Detecting dislodgement of a ventricular lead coupled to an implantable medical device comprises sensing a near-field cardiac EGM via a first electrode of the ventricular lead and a far-field cardiac EGM via a second electrode of the ventricular lead, identifying, R-waves in the near-field cardiac EGM and the far-field cardiac EGM. determining a near-field value of one or more R-wave amplitude metrics based on amplitudes of R-waves identified in the near-field cardiac EGM and a far-field value of the one or more R-wave amplitude metrics based on amplitudes of R-waves identified in the far-field cardiac EGM, detecting dislodgement of the ventricular lead based on at least one of the near-field value or the far-field value of the one or more R-wave amplitude metrics; and providing a lead dislodgment alert in response to detecting the dislodgement of the ventricular lead.

42 Claims, 11 Drawing Sheets

(51) Int. Cl.
*G16H 40/63* (2018.01)
*A61N 1/05* (2006.01)
*A61N 1/372* (2006.01)

(56) References Cited

U.S. PATENT DOCUMENTS

| | | | |
|---|---|---|---|
| 5,713,932 | A | 2/1998 | Gillberg et al. |
| 5,755,736 | A | 5/1998 | Gillberg et al. |
| 5,910,120 | A | 6/1999 | Kim et al. |
| 6,067,469 | A | 5/2000 | Kim et al. |
| 6,195,584 | B1 | 2/2001 | Hill et al. |
| 6,259,947 | B1 | 7/2001 | Olson et al. |
| 6,445,952 | B1 | 9/2002 | Manrodt et al. |
| 6,807,439 | B2 | 10/2004 | Edwards et al. |
| 6,980,860 | B2 | 12/2005 | Stadler et al. |
| 7,167,747 | B2 | 1/2007 | Gunderson et al. |
| 7,333,855 | B2 | 2/2008 | Gunderson et al. |
| 7,664,550 | B2 | 2/2010 | Eick et al. |
| 8,078,277 | B2 | 12/2011 | Gunderson et al. |
| 8,660,643 | B2 | 2/2014 | Gunderson |
| 8,781,585 | B2 | 7/2014 | Gunderson et al. |
| 9,486,155 | B2 | 11/2016 | Sarkar et al. |
| 9,572,990 | B2 | 2/2017 | Gunderson |
| 2004/0220631 | A1 | 11/2004 | Burnes et al. |
| 2004/0225332 | A1* | 11/2004 | Gebhardt ............ A61N 1/3622 607/17 |
| 2011/0034983 | A1 | 2/2011 | Min et al. |
| 2012/0143278 | A1* | 6/2012 | Ryu ............ A61B 5/04525 607/28 |
| 2013/0079861 | A1 | 3/2013 | Reinert et al. |
| 2014/0018873 | A1 | 1/2014 | Gunderson |
| 2014/0350422 | A1 | 11/2014 | Stewart |
| 2016/0235992 | A1 | 8/2016 | Sarker et al. |
| 2016/0375239 | A1 | 12/2016 | Swerdlow |
| 2017/0274204 | A1 | 9/2017 | Gunderson |
| 2019/0091469 | A1 | 3/2019 | Gunderson |

OTHER PUBLICATIONS

Iwasawa, et al., "Discrimination Algorithm of an Implantable Cardioverter Defibrillator in a Case with a Lead Dislodgement," Heart Rhythm, vol. 11, 2014, PO05-208, Abstract, 2 pp.
Ruiz-Salas et al., "Inappropriate Shock Due to Late Dislocation of Electrode," International Journal of Cardiology, vol. 199, 2015, 3 pp.
Veltmann, et al., "Fatal Inappropriate ICD Shock," J. Cardiovasc. Electrophysiol. vol. 18(3), 2007, 3 pp.
Cheng et al., "Acute Lead Dislodgements and In-Hospital Mortality in Patients Enrolled in the National Cardiovascula Data Registry Implantable Cardioverter Defibrillator Registry", Journal of American College of Cardiology, vol. 56, No. 20, 2010, 6 pages.
Ghani et al, "Incidence of Lead Dislodgement, Malfunction and Perforation During the First Year Following Device Implantation", Neth Heart Journal, vol. 22, 2014, 6 pages.
Zaman et al., "Early Diagnosis of Defibrillation Lead Dislodgement", JACC: Clinical Electrophysiology, 2018, 14 pages.
International Search Report and Written Opinion from International Application No. PCT/US2017/065389, dated Apr. 16, 2018, 12 pp.
Pellman et al., "Atrial Fibrillation: Mechanisms, Therapeutics, and Future Directions," Comprehensive Physiology, vol. 5, No. 2, Apr. 2015, pp. 649-665.
Desimone et al., "Supraventricular Arrhythmias: Clinical Framework and Common Scenarios for the Internist," Mayo Clinic Proceedings, vol. 93, No. 12, Dec. 2018, 1825-1841.

\* cited by examiner

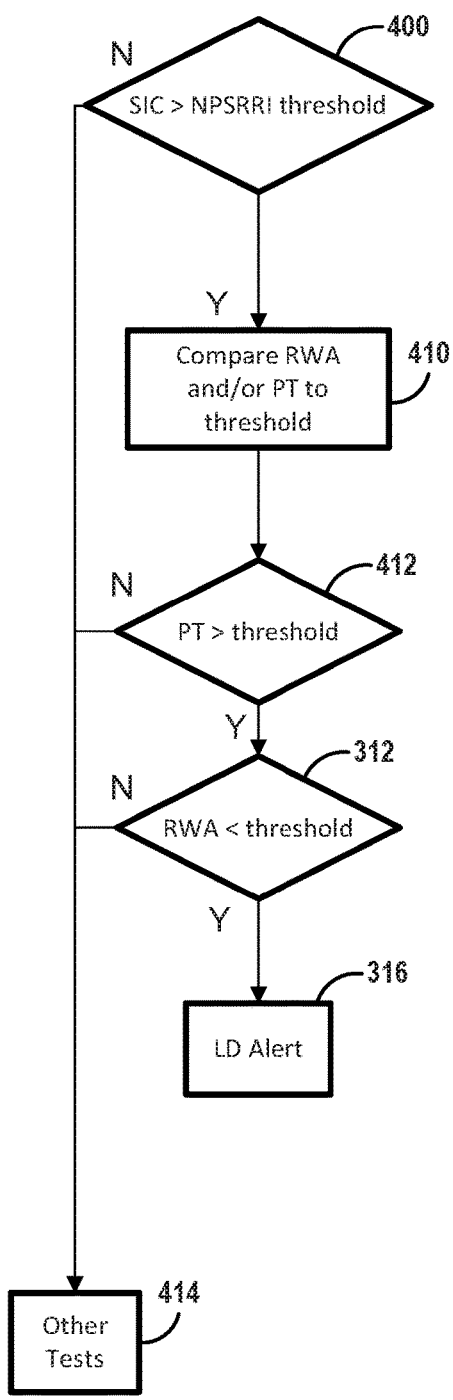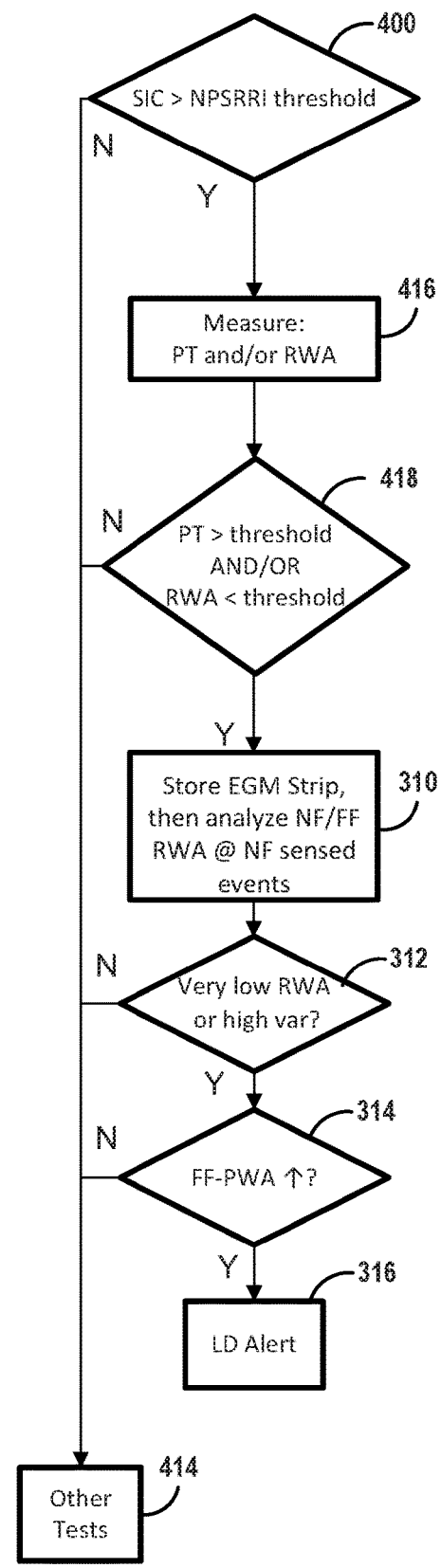
FIG. 11A
FIG. 11B

DETECTING VENTRICULAR LEAD DISLODGEMENT

This application claims the benefit of U.S. Provisional Application Ser. No. 62/432,504, filed Dec. 9, 2016, the entire content of which is incorporated herein by reference.

TECHNICAL FIELD

The disclosure relates generally to medical devices and, more particularly, to a medical device, medical device system and method for detecting dislodgment of a ventricular lead.

BACKGROUND

Implantable medical devices (IMDs), including pacemakers and implantable cardioverter-defibrillators (ICDs), record cardiac electrogram (EGM) signals for sensing cardiac events, e.g., P-waves and R-waves. Episodes of bradycardia, tachycardia and/or fibrillation are detected from the sensed cardiac events and responded to as needed with pacing therapy or high-voltage cardioversion/defibrillation therapy. Reliable detection and treatment of potentially life-threatening ventricular tachycardia (VT) and ventricular fibrillation (VF) requires reliable sensing of cardiac signals.

Dislodgement or dislocation of a cardiac lead carrying electrodes for sensing EGM signals reduces reliable sensing and could result in erroneous sensing of cardiac signals, leading to improper detection of the cardiac rhythm and inappropriate delivery or withholding of pacing or shock therapy. While an occurrence of ventricular lead dislodgement is rare, such dislodgement could potentially cause inappropriate shock therapy to be delivered. For example, in some rare instances of a ventricular lead dislodging or being dislodged during an episode of sinus tachycardia or atrial fibrillation, atrial cardiac signals associated with the episode may be inappropriately sensed as ventricular signals, causing inappropriate detection of a ventricular fibrillation episode and the resultant delivery of high-voltage anti-tachyarrhythmia therapy. In some cases, a dislodged lead may cause a necessary or optimal therapy, such as bradycardia pacing, anti-tachycardia pacing, or anti-tachyarrhythmia shock, to not be effective because the therapy electrodes moved from the implanted location. Accordingly, it is desirable to provide an implantable medical device and associated medical device system that is capable of detecting ventricular lead dislodgement.

SUMMARY

Devices, systems, and techniques for identifying dislodgment of a ventricular lead are described in this disclosure. When a ventricular lead is dislodged, one or more characteristics of one or both of a near-field cardiac EGM and a far-field cardiac EGM sensed via the ventricular lead may change in a detectable manner. For example, in one or both of the EGMs, the amplitudes of R-waves may be relatively low and/or variable, the amplitudes of P-waves detected in the ventricular EGM may increase and be variable, the variability of the RR intervals may be relatively high, and/or the RR intervals may exhibit a pattern, which may include alternating lengths, such as a short-long-short-long (SLSL) pattern. The techniques of this disclosure may include detecting dislodgement of the ventricular lead based on such characteristics.

In one example, the techniques of this disclosure are directed to a method of detecting dislodgement of a ventricular lead coupled to an implantable medical device, the method comprising: sensing, by the implantable medical device, a near-field cardiac electrogram (EGM) via the ventricular lead; identifying, by processing circuitry, R-waves in the near-field EGM; determining, by the processing circuitry, a variability of amplitudes of R-waves identified in the near-field EGM; detecting, by the processing circuitry, dislodgement of the ventricular lead based on the variability of the amplitudes of the R-waves; and providing, by the processing circuitry, a lead dislodgment alert in response to detecting the dislodgement of the ventricular lead.

In another example, the techniques of this disclosure are directed to a medical device system comprising: a ventricular lead; an implantable medical device coupled to the ventricular lead and configured to sense a near-field cardiac electrogram (EGM) via the ventricular lead; and processing circuitry configured to: identify R-waves in the near-field EGM; determine a variability of amplitudes of R-waves identified in the near-field EGM; detect dislodgement of the ventricular lead based on the variability of the amplitudes of the R-waves; and provide a lead dislodgment alert in response to detecting the dislodgement of the ventricular lead.

In another example, the techniques of this disclosure are directed to a medical device system comprising: means for sensing a near-field cardiac electrogram (EGM) via the ventricular lead; means for identifying R-waves in the near-field EGM; means for determining a variability of amplitudes of R-waves identified in the near-field EGM; means for detecting dislodgement of the ventricular lead based on the variability of the amplitudes of the R-waves; and means for providing a lead dislodgment alert in response to detecting the dislodgement of the ventricular lead In another example, the techniques of this disclosure are directed to a non-transitory computer-readable storage medium comprising program instructions that, when executed by processing circuitry of a medical device system, cause the processing circuitry to: identify R-waves in a near-field cardiac electrogram (EGM) sensed by an implantable medical device via a ventricular lead; determine a variability of amplitudes of R-waves identified in the near-field EGM; detect dislodgement of the ventricular lead based on the variability of the amplitudes of the R-waves; and provide a lead dislodgment alert in response to detecting the dislodgement of the ventricular lead.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

FIG. 11A is a flowchart of another example technique for identifying dislodgment of a ventricular lead including triggering a comparison of stored performance measurements to a predetermined threshold.

FIG. 11B is a flowchart of another example technique for identifying dislodgment of a ventricular lead including triggering other performance measurements.

DETAILED DESCRIPTION

As described above, methods, devices, and systems for identifying dislodgment of a ventricular lead are described in this disclosure. In the following description, references are made to illustrative examples. It is understood that other examples may be utilized without departing from the scope of the disclosure.

Figure 1:
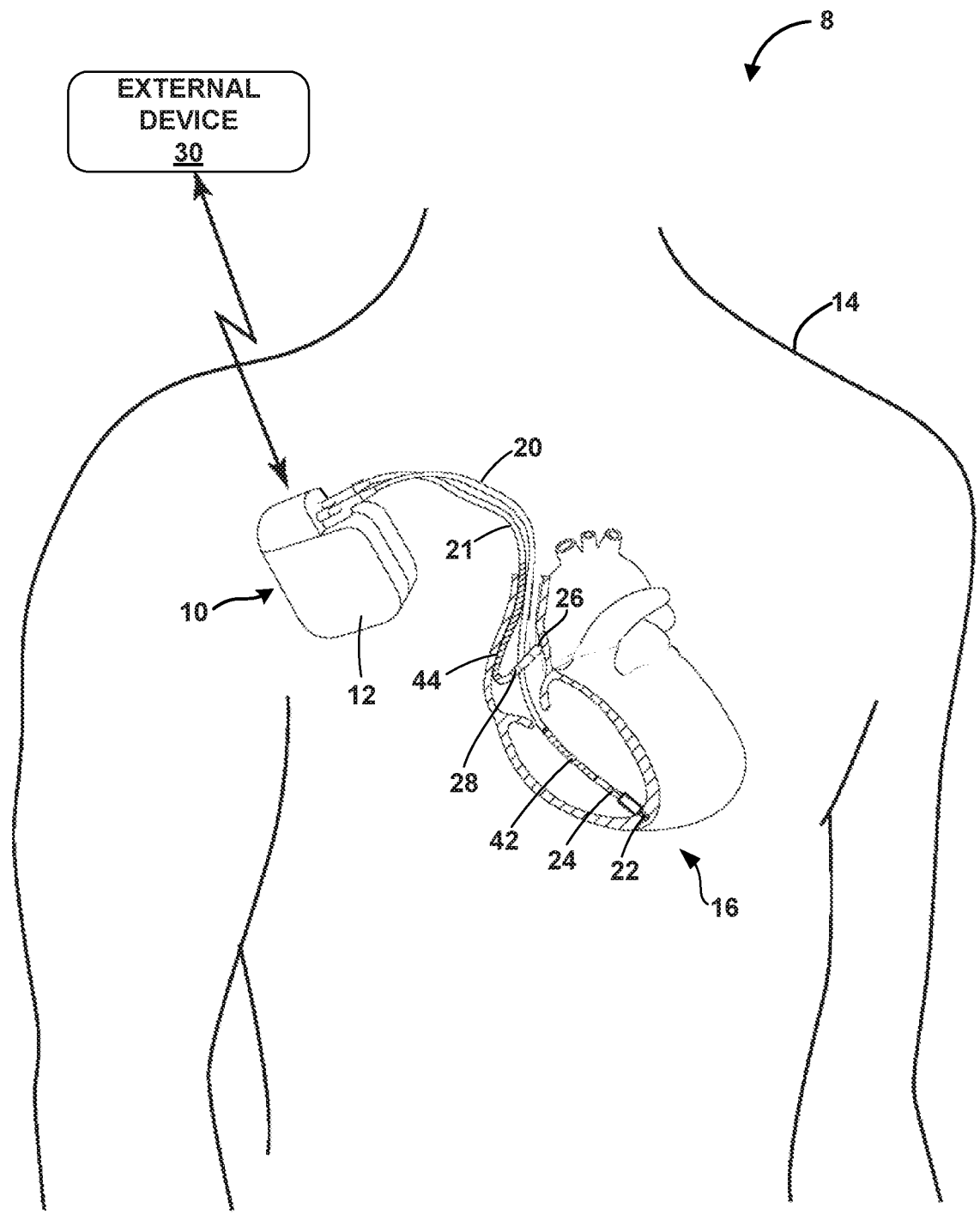
FIG. 1 is an example schematic diagram of an implantable medical device system configured to detect dislodgement of a ventricular lead.

FIG. 1 is an example schematic diagram of an implantable medical device system configured to detect dislodgement of a ventricular lead. As illustrated in FIG. 1, a medical device system 8 for sensing cardiac events (e.g., P-waves and R-waves) and detecting tachyarrhythmia episodes, as well as detecting dislodgement of a ventricular lead, may include an implantable medical device (IMD) 10, a ventricular lead 20 and an atrial lead 21. In one example, IMD 10 may be an implantable cardioverter-defibrillator (ICD) capable of delivering pacing, cardioversion and defibrillation therapy to the heart 16 of a patient 14. In other examples, IMD 10 may be a pacemaker capable of delivering pacing therapy, including anti-tachycardia pacing (ATP) to the patient, but need not include the capability of delivering cardioversion or defibrillation therapies.

Ventricular lead 20 and atrial lead 21 are electrically coupled to IMD 10 and extend into the patient's heart 16. Ventricular lead 20 includes electrodes 22 and 24 shown positioned on the lead in the patient's right ventricle (RV) for sensing ventricular EGM signals and pacing in the RV. Atrial lead 21 includes electrodes 26 and 28 positioned on the lead in the patient's right atrium (RA) for sensing atrial EGM signals and pacing in the RA. Such a medical device and medical device system is described, for example, in commonly assigned U.S. Patent Publication No. 2014/0018873 (hereinafter "the '873 publication") and U.S. Patent Publication No. 2016/0375239, filed on Feb. 2, 2016 by Lambda Nu Technology LLC (hereinafter "the '239 publication"), which are incorporated herein by reference in their entireties.

In the example of FIG. 1, ventricular lead 20 additionally carries a high voltage coil electrode 42, and atrial lead 21 carries a high voltage coil electrode 44, used to deliver cardioversion and defibrillation shock pulses. In other examples, ventricular lead 20 may carry both of high voltage coil electrodes 42 and 44, or may carry a high voltage coil electrode in addition to those illustrated in the example of FIG. 1. Both ventricular lead 20 and atrial lead 21 may be used to acquire cardiac EGM signals from patient 14 and to deliver therapy in response to the acquired data. Medical device system 8 is shown as a dual chamber ICD including atrial lead 21 and ventricular lead 20, but in some embodiments, system 8 may be a dual or multi-chamber system including a coronary sinus lead extending into the right atrium, through the coronary sinus and into a cardiac vein to position electrodes along the left ventricle (LV) for sensing LV EGM signals and delivering pacing pulses to the LV. In some examples, system 8 may be a single chamber system, or otherwise not include atrial lead 21.

In some examples, ventricular lead 20 is anchored along the right ventricular apex or the intraventricular septum by a fixation member (not shown), such as tines positioned at the distal end of lead 20 in the vicinity of electrode 22 or a helical screw, which may also serve as electrode 22. Use of a fixation member generally anchors the position of ventricular lead 20 in the RV. However, on rare occasions, ventricular lead 20 may become dislodged from the ventricular myocardium and shift or migrate within the ventricle or toward or within the right atrium. In other words, ventricular lead dislodgement may include any dislodgement of the ventricular lead, including dislodgement from an original implant location into another location in the ventricular chamber, as well as dislodgment from the ventricular chamber into atrial chamber.

When dislodgement occurs, EGM signals received by IMD 10 via ventricular lead 20 from different vectors including one or more of electrodes 22, 24, and 42 will change due to the altered location of the electrodes in the heart, which may (in some cases) result in electrical activity of the atria of heart being inadvertently sensed via ventricular lead 20 as ventricular activity. Such a situation of sensing both atrial and ventricular depolarizations as ventricular signals can be especially problematic during the occurrence of atrial fibrillation (AF). In an example where the ventricular lead senses AF, IMD 10 may incorrectly determine that the sensed AF on ventricular lead 20 is ventricular fibrillation (VF) or some other form of ventricular tachycardia (VT). Therefore, the result of sensing AF on ventricular lead 20 could be inappropriate detection of a VF episode and unnecessary delivery of ventricular defibrillation therapy. Techniques for detecting cardiac lead dislodgement, including dislodgement of a ventricular lead during the occurrence of atrial fibrillation or sinus tachycardia, will be described herein.

Implantable medical device circuitry configured for performing the methods described herein and an associated battery or batteries are housed within a sealed housing 12. Housing 12 may be conductive so as to serve as an electrode for use as an indifferent electrode during pacing or sensing or as an active electrode during defibrillation. As such, housing 12 is also referred to herein as "housing electrode" 12. In other examples, an indifferent electrode may be separate from housing 12 and placed elsewhere on IMD 10, such as in the header.

EGM signal data, cardiac rhythm episode data, and lead dislodgement data acquired by IMD 10 can be transmitted to an external device 30. External device 30 may be a computing device, e.g., used in a home, ambulatory, clinic, or hospital setting, to communicate with IMD 10 via wireless telemetry. External device 30 may be coupled to a remote patient monitoring system, such as Carelink®, available from Medtronic plc, of Dublin, Ireland. External device 30 may be, as examples, a programmer, external monitor, or consumer device, e.g., smart phone.

External device 30 may be used to program commands or operating parameters into IMD 10 for controlling IMD function, e.g., when configured as a programmer for IMD 10. External device 30 may be used to interrogate IMD 10 to retrieve data, including device operational data as well as physiological data accumulated in IMD memory. The interrogation may be automatic, e.g., according to a schedule, or in response to a remote or local user command. Programmers, external monitors, and consumer devices are examples of external devices 30 that may be used to interrogate IMD 10. Examples of communication techniques used by IMD 10 and external device 30 include radiofrequency (RF) telemetry, which may be an RF link established via Bluetooth, WiFi, or medical implant communication service (MICS).

In some examples, the term "near-field" may refer to an EGM recorded by two or more electrodes located in proximity to the source signal for the EGM. For example, a near-field electrogram (NF-EGM) in the ventricle may be recorded from two electrodes, e.g., closely-spaced electrodes near the tip of the lead, positioned on or within the ventricle. At least one of the electrodes may be a small sensing electrode at the tip of the lead. Because these electrodes for a NF-EGM may be closely spaced, their electrical "field of view" may be short-range and dominated by the electrical signals originating in myocardium adjacent to the electrodes, such as the lead tip. The NF-EGM may have advantages for sensing local myocardial electrical activity, and IMDs, such as an ICD or pacemaker, may monitor the NF-EGM continuously to sense cardiac rhythm. As one example, a NF-EGM may be obtained by sensing between tip electrode 22 and coil electrode 44, or between tip electrode 22 and ring electrode 24 of ventricular lead 20.

A far-field electrogram (FF-EGM) may include an EGM recorded by one or more electrodes located at a distance from the source of the EGM. In some examples, a ventricular FF-EGM may record ventricular activation using at least one electrode that is not in a ventricle. In some examples, the ventricular FF-EGM may refer to an EGM recorded between two or more large, widely-spaced electrodes. In some examples, electrodes may be separated by a distance of 10 centimeters (cm) or more. Some examples of widely spaced electrodes may include electrodes used to deliver defibrillation shocks, such as coil electrodes 42 and 44, housing electrode 12, and (in in the example dual-coil defibrillation leads), a proximal defibrillation coil and distal defibrillation coil (not shown in FIG. 1). As one specific example, a far-field electrogram (FF-EGM) may be obtained by sensing between coil electrode 42 and housing electrode 12. In some examples a FF-EGM may be referred to as the "shock" EGM recorded between two or among three widely-spaced, large shock electrodes.

The FF-EGM may record a more global signal than the NF-EGM. In some examples, an IMD may analyze a FF-EGM to perform a secondary function that is activated only after analysis of the sensed NF-EGM indicates that VT or VF is present. This secondary function may confirm the presence of VT or VF as indicated by the NF-EGM sensing channel. In some examples patterns, waveforms, or morphology may be visible on NF-EGM and not on the FF-EGM, and vice versa. The techniques of this disclosure may have advantages in detecting lead dislodgement by combining and comparing specific parameters on either or both the near-field and far-field sensing to determine lead dislodgement under a variety of conditions, while minimizing the possibility of a false indication of dislodgement.

One or more components of system 8 may identify dislodgment of ventricular lead 20 using the techniques described in this disclosure. For example, IMD 10 may sense a ventricular EGM via ventricular lead 20, e.g., a near-field EGM sensed via tip electrode 22 and ring electrode 24 of ventricular lead 20, or a far-field EGM via housing 12 and high voltage coil electrode 42 (and/or in some cases high voltage coil electrode 44) on the ventricular lead. Other examples of far-field cardiac EGMs will be described in more detail below. One or more of IMD 10 and external device 30 may determine whether ventricular lead 20 is dislodged based on the near-field and/or far-field EGM. External device 30 may receive the EGM(s) and/or data representative of the EGM(s) from IMD 10 via RF telemetry.

For example, IMD 10 or external device 30 may identify one or more characteristics of one or both of the near-field and far-field EGM that are associated with the dislodgement of ventricular lead 20, such as amplitudes of R-waves that are relatively low and/or variable, increased amplitudes of P-waves detected in the ventricular EGM, relatively high variability of the RR intervals, and/or RR intervals that exhibit a pattern, which may include alternating lengths, such as a short-long-short-long (SLSL) pattern. IMD 10 or external device 30 may detect dislodgement of ventricular lead 20 based on such characteristics meeting one or more respective thresholds. IMD 10 and/or external device 30 may provide a lead dislodgement alert in response to detecting dislodgement of ventricular lead 20. In some examples, IMD 10 may alter its sensing or therapy delivery, such as withholding a ventricular defibrillation therapy, in response to detecting dislodgement of ventricular lead 20.

EGM signals may be sensed in real-time and/or recorded in the memory of medical device 10 to be analyzed. In some examples, real-time sensed events may trigger medical device 10 to store a near-field and/or a far-field EGM, e.g., detection of VT or VF may trigger medical device 10 to store one or more EGMs. For example, medical device 10 does not need to store an EGM to measure an RR interval. RR intervals can be determined with real-time sensing using one electrode configuration, such as tip-ring, and also determined from a stored EGM using a different set of electrodes (e.g. RVcoil-Can). The various metrics described herein may likewise be determined based on real-time and/or stored EGMs.

Figure 2:
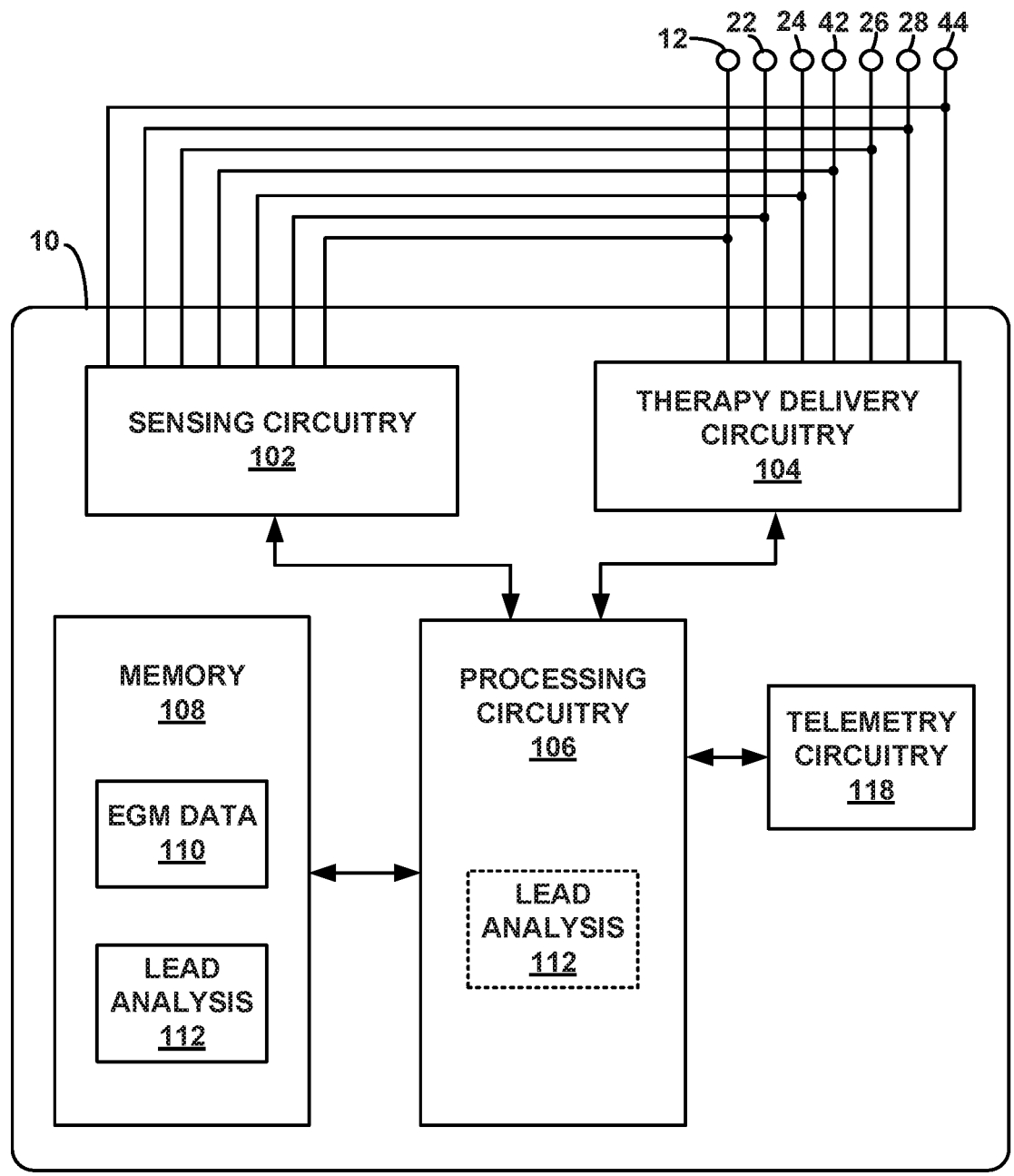
FIG. 2 is a functional block diagram of an example implantable medical device configured to detect dislodgement of a ventricular lead.

FIG. 2 is a functional block diagram of an example configuration of IMD 10 that detects dislodgement of a ventricular lead, e.g., ventricular lead 20 of FIG. 1. In the example illustrated by FIG. 2, IMD 10 includes sensing circuitry 102, therapy delivery circuitry 104, processing circuitry 106, associated memory 108, and telemetry circuitry 118.

Processing circuitry 106 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 106 may include multiple components, such as any combination of one or more microprocessors, one or more DSPs, one or more ASICs, or one or more FPGAs, as well as other discrete or integrated logic circuitry, and/or analog circuitry.

Memory 108 may store program instructions, which may include one or more program modules, which are executable by processing circuitry 106. When executed by processing circuitry 106, such program instructions may cause processing circuitry 106 and IMD 10 to provide the functionality ascribed to them herein. The program instructions may be embodied in software, firmware and/or RAMware. Memory 108 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Sensing circuitry 102 is configured to receive cardiac electrical signals from selected combinations of two or more of electrodes 22, 24, 26, 28, 42 and 44 carried by the ventricular lead 20 and atrial lead 21, along with housing electrode 12. Sensing circuitry 102 is configured to sense cardiac events attendant to the depolarization of myocardial tissue, e.g. P-waves and R-waves. Sensing circuitry 102 may include a switching circuitry for selectively coupling electrodes 12, 22, 24, 26, 28, 42, 44 to sensing circuitry 102 in order to monitor electrical activity of heart 16. In other examples, not shown in FIG. 2, sensing circuitry 102 may receive cardiac electrical signals from other electrodes such as one or more LV electrodes, as described above in relation to FIG. 1. The switching circuitry may include a switch array, switch matrix, multiplexer, or any other type of switching device suitable to selectively couple one or more of the electrodes to sensing circuitry 102. In some examples, processing circuitry 106 selects the electrodes to function as sense electrodes, or the sensing vector, via the switching circuitry within sensing circuitry 102.

Sensing circuitry 102 may include multiple sensing channels, each of which may be selectively coupled to respective combinations of electrodes 12, 22, 24, 26, 28, 42, 44 to detect electrical activity of a particular chamber of heart 16, e.g., an atrial sensing channel and one or more ventricular sensing channels. Each sensing channel may be configured to amplify, filter and rectify the cardiac electrical signal received from selected electrodes coupled to the respective sensing channel to detect cardiac events, e.g., P-waves and/or R-waves. For example, each sensing channel may include one or more filters and amplifiers for filtering and amplifying a signal received from a selected pair of electrodes. The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter.

Sensing circuitry 102 outputs an indication to processing circuitry 106 in response to sensing of a cardiac event, in the respective chamber of heart 16 (e.g., detected P-waves or R-waves). In this manner, processing circuitry 106 may receive detected cardiac event signals corresponding to the occurrence of detected R-waves and P-waves in the respective chambers of heart 16. Indications of detected R-waves and P-waves may be used for detecting ventricular and/or atrial tachyarrhythmia episodes, e.g., ventricular or atrial fibrillation episodes. Sensing circuitry 102 may also pass one or more digitized EGM signals to processing circuitry 106 for analysis, e.g., for use in cardiac rhythm discrimination. Processing circuitry 106 may use the indications of R-waves and/or the digitized ventricular EGM signals to detect dislodgement of ventricular lead 20 according to the techniques described herein. Indications of R-wave and P-wave timing, as well as digitized EGMs, may be stored in memory 108 as EGM data 110.

Memory 108 may also store a lead analysis module 112. Lead analysis module 112 may be a software, firmware, or RAMware module executable by processing circuitry 106 to cause processing circuitry 106 to provide functionality related to identifying dislodgement of ventricular lead 20 during atrial fibrillation as described herein. Such functionality may include identifying characteristics of near-field and far-field ventricular EGM signals, detecting dislodgment based on the characteristics, providing an alert, and/or modifying sensing or therapy provided by IMD 10, as described herein. Processing circuitry 106 may load lead analysis module 112 from memory 108 (shown by the dotted lead analysis module 112 within processing circuitry 106) and execute the loaded lead analysis module 112 in response to an event, such as detection of atrial fibrillation via an atrial EGM, or a command from external device 30 received via telemetry circuitry 118. In other examples, processing circuitry 106 may execute lead analysis module 112 periodically, e.g., according to a schedule, or substantially continuously, throughout the operation of IMD 10.

Processing circuitry 106 may control therapy delivery circuitry 104 to deliver electrical therapy, e.g., cardiac pacing, anti-tachyarrhythmia therapy, or cardioversion or defibrillation shock pulses, to heart 16 according to therapy parameters stored in memory 108. Therapy delivery circuitry 104 is electrically coupled to electrodes 12, 22, 24, 26, 28, 42, 44, and is configured to generate and deliver electrical therapy to heart 16 via selected combinations of electrodes 12, 22, 24, 26, 28, 42, 44. Therapy delivery circuit 104 may include charging circuitry, one or more charge storage devices, such as one or more high voltage capacitors and/or one or more low voltage capacitors, and switching circuitry that controls when the capacitor(s) are discharged to selected combinations of electrodes 12, 22, 24, 26, 28, 42, 44. Charging of capacitors to a programmed pulse amplitude and discharging of the capacitors for a programmed pulse width may be performed by therapy delivery circuit 104 according to control signals received from processing circuitry 106.

Memory 108 stores intervals, counters, or other data used by processing circuitry 106 to control the delivery of pacing pulses by therapy delivery circuitry 104. Such data may include intervals and counters used by processing circuitry 106 to control the delivery of pacing pulses to heart 16. The intervals and/or counters are, in some examples, used by processing circuitry 106 to control the timing of delivery of pacing pulses relative to an intrinsic or paced event in another chamber. Memory 108 also stores intervals for controlling cardiac sensing functions such as blanking intervals and refractory sensing intervals and counters for counting sensed events for detecting cardiac rhythm episodes. Events sensed by sense amplifiers included in sensing circuitry 102 are identified in part based on their occurrence outside a blanking interval and inside or outside of a refractory sensing interval. Events that occur within predetermined interval ranges are counted for detecting cardiac rhythms. According to embodiments described herein, sensing circuitry 102, therapy circuitry 104, memory 108, and processing circuitry 106 are configured to use timers and counters for measuring sensed event intervals and determining event patterns for use in detecting possible ventricular lead dislodgement.

Processing circuitry 106 may receive analog and/or digitized EGM signals and sensed event signals corresponding to detected R-waves and P-waves from sensing circuitry 102 for use in identifying possible dislodgement or dislocation of ventricular lead 20, e.g., when executing lead analysis module 112. As will be described herein, processing circuitry 106 may detect dislodgement of ventricular lead 20 based on an amplitude of the ventricular EGM signal, e.g., an amplitude of R-waves in the digitized ventricular EGM, and/or variability of RR intervals indicated by the sensing of R-waves by sensing circuitry 102.

In some examples, processing circuitry 106 may analyze a near-field and far-field EGM channel to determine R-wave amplitude (RWA), RR variability and other factors described in more detail below. In some examples, processing circuitry 106 may combine other algorithms and techniques with the techniques of this disclosure. For example, in a dual chamber device, processor 106 may confirm measurements indicating a lead dislodgement by analyzing cardiac signals on the atrial channel, e.g., as described in the above-incorporated '239 publication.

In some examples, processing circuitry 106 may analyze RR intervals for short-long patterns, e.g., as described in the above-incorporated '873 publication and '239 publication. For example, the '873 publication teaches detection of lead dislodgement to the atrium by the recording of short-long-short-long (SLSL) sequences of intervals between NF-EGM signals. The "short" interval may correspond to the P-R interval; the "long" may correspond to the R-P interval. Additionally, the algorithm may require that each signal have a relatively low amplitude (e.g., 0.5-2.5 mV) and that a zero crossing occurs in the short interval to exclude R-wave double-counting. This algorithm may alert when two such sequences occur.

In more detail, the sensed event intervals, e.g., RR intervals, are monitored to detect an event interval pattern that is characteristic of lead dislodgement but distinguishes lead dislodgement from a tachyarrhythmia event pattern. In one embodiment, processing circuitry 106 may determine if two sequences of a short-long-short-long (SLSL) event interval pattern are detected. If the ventricular lead 20 has become dislodged and migrated such that electrodes 22 and 24 are closer to the right atrium, both P-waves and R-waves may be sensed by electrodes 22 and 24. Both the P-waves and the R-waves will be sensed as "R-waves" by sensing circuitry 102 since electrodes 22 and 24 of RV lead 20 will be coupled to a ventricular sensing channel. A P-wave sensed as an R-wave followed by a true R-wave will result in a short, false "RR" interval being measured followed by a long RR interval. The long RR interval may be a true RR interval, or it may be an interval between a true R-wave the next P-wave falsely sensed as an R-wave.

In the case of lead dislodgement, an event interval pattern represented by a consecutive sequence of SLSL intervals followed by a second sequence of SLSL intervals may be evidence of possible lead dislodgement. The two SLSL sequences may occur consecutively or non-consecutively, but the SLSL interval pattern that occurs within a single sequence are consecutive short and long intervals. In general, a criterion for detecting an interval pattern sequence that includes at least one short-long pair or RR intervals is used to detect a first indication of possible lead dislodgement.

A definition of a short interval and a definition of a long interval may be established and stored in memory 108 and used by processing circuitry 106 to detect the SLSL sequences. In one embodiment, a short interval is defined as an interval that is between approximately 120 ms and 250 ms long. The short interval is defined to correspond approximately to an expected P-R interval. The long interval may be defined in ms or as a multiple of the short interval. For example, a long interval may be required to be at least 1.5 times longer than a short interval.

In some examples, processing circuitry 106 may check whether short-long patterns exceed a threshold. The threshold may be, for example, a threshold consecutive number of SL interval pairs, or a threshold number of SL interval pairs over a period of time. In some examples, for a group of R-waves, e.g., 18 R-waves, processing circuitry 106 may check whether any two consecutive RR intervals add up to a value greater than 450 ms +/−5%, as described, for example, in the '239 publication. As used herein, exceeding a threshold may refer to either a value being greater than or equal to a threshold value, or a value being less than or equal to the threshold value. In other words, exceeding a threshold value may refer to satisfying the threshold by crossing a threshold value (e.g., from normal to abnormal) in either direction, depending on the particular threshold and criteria for satisfaction.

In some examples, the techniques of this disclosure may be combined with other arrhythmia discrimination techniques, or lead or sensing integrity issue discrimination techniques, such as those that identify T-wave over-sensing, e.g., as described in the above-incorporated '239 publication. In some examples, the techniques of this disclosure may be combined with other lead dislodgement detection techniques, such as those described in U.S. Pat. No. 9,572,990 by Gunderson, the '239 publication, or the 873 publication.

Processing circuitry 106 may respond to a lead dislodgement by generating a patient or clinician alert, which may be transmitted by telemetry circuitry 118, by withholding detection of ventricular fibrillation and/or delivery of defibrillation therapy, or both, as will be described below. Processing circuitry 106 may additionally respond to a possible lead dislodgement by adjusting cardiac rhythm episode detection criteria and/or adjusting the control of therapy delivery module 104 to avoid inappropriate delivery or withholding of a therapy.

Telemetry circuitry 118 is used to communicate with external device 30, for transmitting data accumulated by IMD 10 and for receiving interrogation and programming commands from external device 30. Under the control of processing circuitry 106, telemetry circuitry 118 may transmit an alert to notify a clinician and/or the patient that IMD 10 has detected a possible ventricular lead dislodgement. This alert enables the clinician to perform additional testing to confirm the dislodgement and to intervene if necessary to reposition or replace the lead, or to prevent unnecessary defibrillation therapy from being delivered to the patient. In other embodiments, IMD 10 may be equipped with alert circuitry configured to emit a sensory alert perceptible by the patient, e.g. a vibration or an audible tone, under the control of processing circuitry 106 to alert the patient to the possibility of a ventricular lead dislodgement.

As described above, in instances of a ventricular lead dislodging or being dislodged, the ventricular lead may migrate from the ventricle towards the atrium, increasing the likelihood that cardiac signals of the atrium, (e.g., atrial cardiac events), which in some cases may be associated with a sinus tachycardia or the atrial fibrillation episode may be inappropriately sensed as ventricular events, causing inappropriate sensing of a ventricular tachyarrhythmia episode, such as ventricular fibrillation, and resulting in an inappropriate delivery of ventricular fibrillation therapy. Accordingly, in some examples, processing circuitry 106 may control therapy delivery circuitry 104 to withhold the delivery of a therapy for treating ventricular arrhythmias, e.g., a ventricular defibrillation shock for treating a detected ventricular fibrillation episode, based on detecting dislodgement of ventricular lead 20. In some examples, processing circuitry 106 determines characteristics of the ventricular EGM(s) associated with lead dislodgement in response to detection of a ventricular fibrillation episode. If IMD 10 detects a dislodgement of ventricular lead 20, processing circuitry 106 may control therapy delivery circuitry 104 to withhold delivery of a defibrillation shock or some other therapy, such as ATP.

In some examples, processing circuitry 106 initiates the analysis to identify characteristics of the ventricular EGM(s) indicative of dislodgment of ventricular lead dislodgement at the time of implant of ventricular lead 20 in the patient 14, either in response to a command from external device 30, or automatically. Since the likelihood of lead dislodgement occurring is greatest within the first few months after implant, processing circuitry 106 may initiate the lead dislodgement surveillance techniques described herein at the time of implant of ventricular lead 20 in the patient 14. After a predetermined time period subsequent to implant, e.g., after three, four, or six months, as examples, processing circuitry 106 may disable lead dislodgment surveillance either in response to commands from external device 30 and/or automatically.

Figure 3:
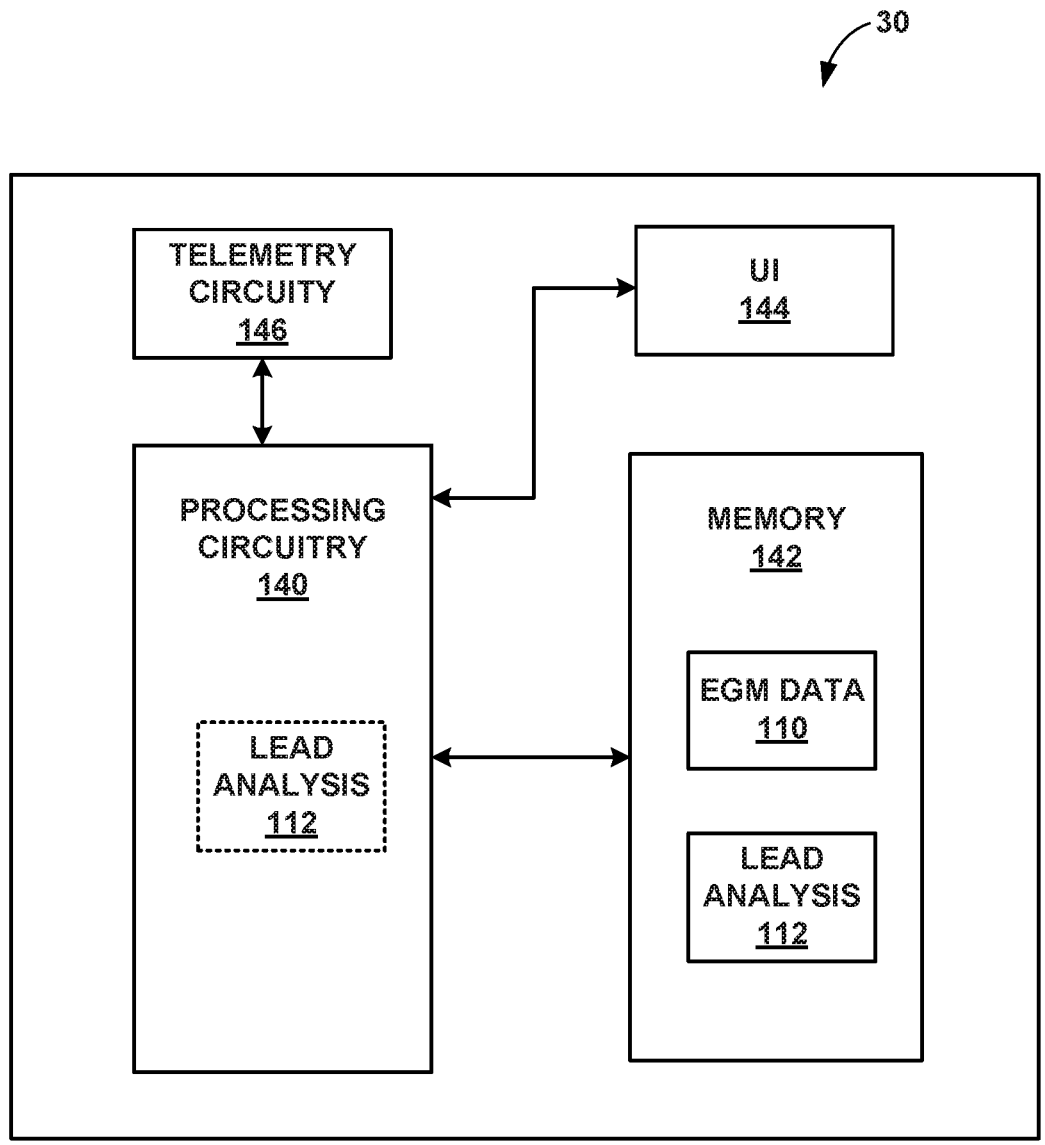
FIG. 3 is a functional block diagram of an example external device configured to communicate with an implantable medical device.

FIG. 3 is a functional block diagram of an example configuration of external device 30. In the example of FIG. 3, external device 30 includes processing circuitry 140, memory 142, user interface (UI) 144, and telemetry circuitry 146. External device 30 may be a dedicated hardware device with dedicated software for the programming and/or interrogation of IMD 10. Alternatively, external device 30 may be an off-the-shelf computing device, e.g., running an application that enables external device 30 to program and/or interrogate IMD 10.

In some examples, a user uses external device 30 to select or program values for operational parameters of IMD 10, e.g., for cardiac sensing, therapy delivery, and lead dislodgment detection. In some examples, a user uses external device 30 to receive data collected by IMD 10, such as cardiac EGM data 110 or other operational and performance data of IMD 10. The user may also receive lead dislodgment alerts provided by IMD 10, or data regarding modifications to sensing or therapy made by IMD 10 in response to detecting lead dislodgement, e.g., indications of when IMD 10 withheld defibrillation therapy, via external device 30. The user may interact with external device 30 via UI 144, which may include a display to present a graphical user interface to a user, and a keypad or another mechanism for receiving input from a user. External device 30 may communicate wirelessly with IMD 10 using telemetry circuitry 146, which may be configured for RF communication with telemetry circuitry 118 of IMD 10.

Processing circuitry 140 may include any combination of integrated circuitry, discrete logic circuitry, analog circuitry, such as one or more microprocessors, DSPs, ASICs, or FPGAs. In some examples, processing circuitry 106 may include multiple components, such as any combination of one or more microprocessors, one or more DSPs, one or more ASICs, or one or more FPGAs, as well as other discrete or integrated logic circuitry, and/or analog circuitry.

Memory 142 may store program instructions, which may include one or more program modules, which are executable by processing circuitry 140. When executed by processing circuitry 140, such program instructions may cause processing circuitry 140 and external device 30 to provide the functionality ascribed to them herein. The program instructions may be embodied in software, firmware and/or RAMware. Memory 142 may include any volatile, non-volatile, magnetic, optical, or electrical media, such as a RAM, ROM, NVRAM, EEPROM, flash memory, or any other digital media.

In some examples, processing circuitry 140 of external device 30 may be configured to provide some or all of the functionality ascribed to processing circuitry 106 of IMD 10 herein. For example, processing circuitry 140 may receive EGM data 110, e.g., of one or more ventricular EGM signal sensed via ventricular lead 20 from IMD 10 via telemetry circuitry 144, and may store the EGM data 110 in memory 142. EGM data 110 may be current EGM data, or data previously collected and stored by IMD 10. Using EGM data 110, processing circuitry 140 of external device 30 may identify characteristics of the ventricular EGM(s) indicative of dislodgment of a ventricular lead, and detect dislodgment of ventricular lead 20 based on such characteristics. Based on the detection of dislodgment, processing circuitry 140 may provide an alert to a user, e.g., via UI 144. In some examples, the lead dislodgment detection functionality may be provided by lead analysis module 112, which may a software module stored in memory 142, and loaded and executed by processing circuitry 140 (as illustrated by the dotted outline lead analysis module 112 within processing circuitry 140), e.g., in response to a command from the user.

Figure 4:
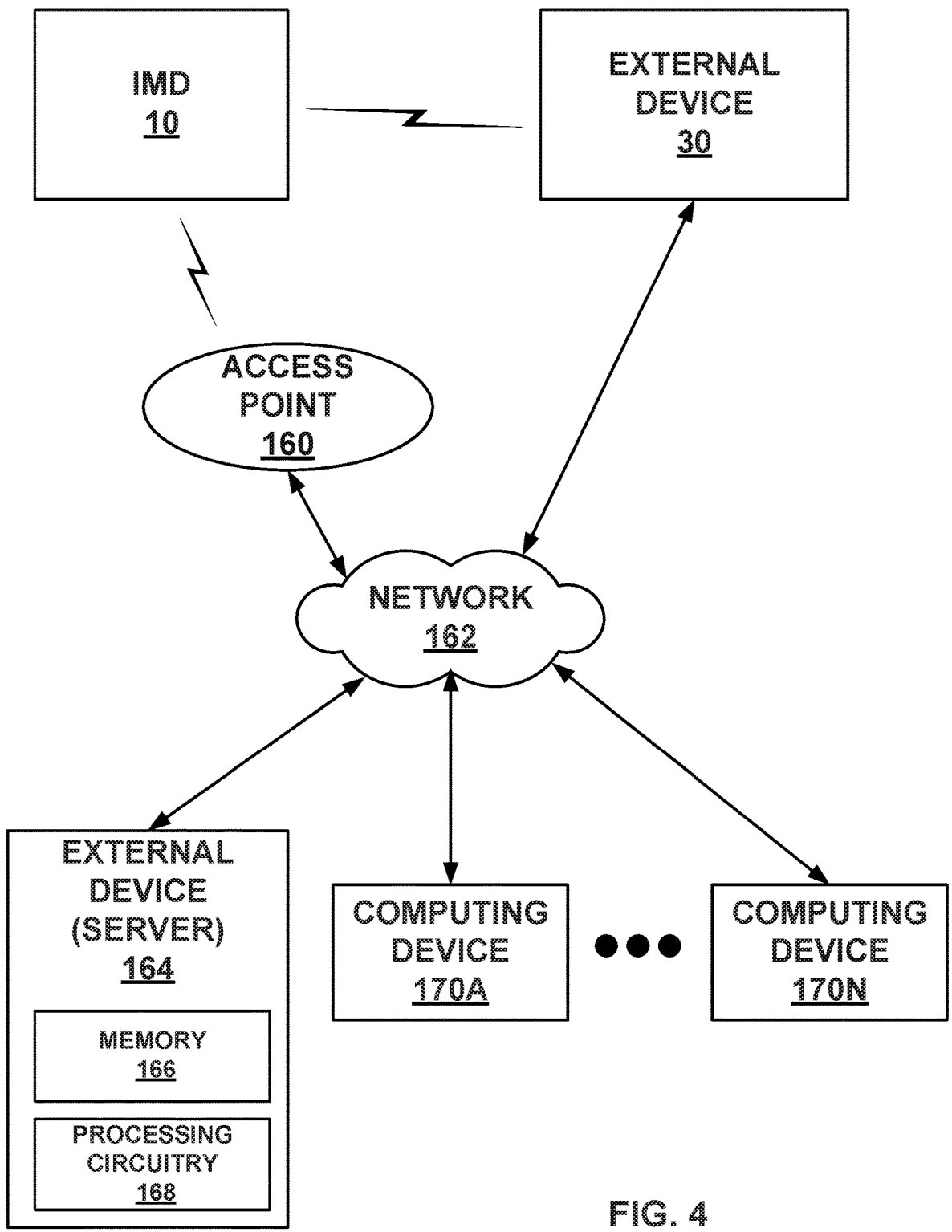
FIG. 4 is a functional block diagram illustrating an example system that includes external computing devices, such as a server and one or more other computing devices, that are coupled to the IMD and programmer shown in FIG. 1 via a network

FIG. 4 is a functional block diagram illustrating an example system that includes external computing devices, such as a server 164 and one or more other computing devices 170A-170N, that are coupled to IMD 10 and external device 30 via a network 162. In this example, IMD 10 may use its telemetry module 118 to, e.g., at different times and/or in different locations or settings, communicate with external device 30 via a first wireless connection, and to communication with an access point 160 via a second wireless connection. In the example of FIG. 4, access point 160, external device 30, server 164, and computing devices 170A-170N are interconnected, and able to communicate with each other, through network 162.

Access point 160 may comprise a device that connects to network 162 via any of a variety of connections, such as telephone dial-up, digital subscriber line (DSL), or cable modem connections. In other examples, access point 160 may be coupled to network 162 through different forms of connections, including wired or wireless connections. In some examples, access point 160 may be co-located with patient 14. Access point 160 may interrogate IMD 10, e.g., periodically or in response to a command from patient 14 or network 162, to retrieve EGM data 110 or other operational data from IMD 10. Access point 160 may provide the retrieved data to server 164 via network 162.

In some cases, server 164 may be configured to provide a secure storage site for data that has been collected from IMD 10 and/or external device 30, such as the Internet. In some cases, server 164 may assemble data in web pages or other documents for viewing by trained professionals, such as clinicians, via computing devices 170A-170N. The illustrated system of FIG. 4 may be implemented, in some aspects, with general network technology and functionality similar to that provided by the Medtronic CareLink® Network developed by Medtronic plc, of Dublin, Ireland.

In some examples, one or more of access point 160, server 164, or computing devices 170 may be configured to perform, e.g., may include processing circuitry configured to perform, some or all of the techniques described herein relating to detecting dislodgment of a ventricular lead. In the example of FIG. 4, server 164 includes a memory 166 to store EGM data received from IMD 10, and processing circuitry 168, which may be configured to provide some or all of the functionality ascribed to processing circuitry 106 of IMD 10 herein. For example, processing circuitry 168 may identify characteristics of the one or more ventricular EGMs indicating dislodgment of a ventricular lead based on the EGM data received from IMD 10. Processing circuitry 168 may identify dislodgment of ventricular lead 20 based on the identified characteristics, and may provide a lead dislodgment alert to a user, e.g., via external device 30 or one of computing devices 170.

Figure 5:
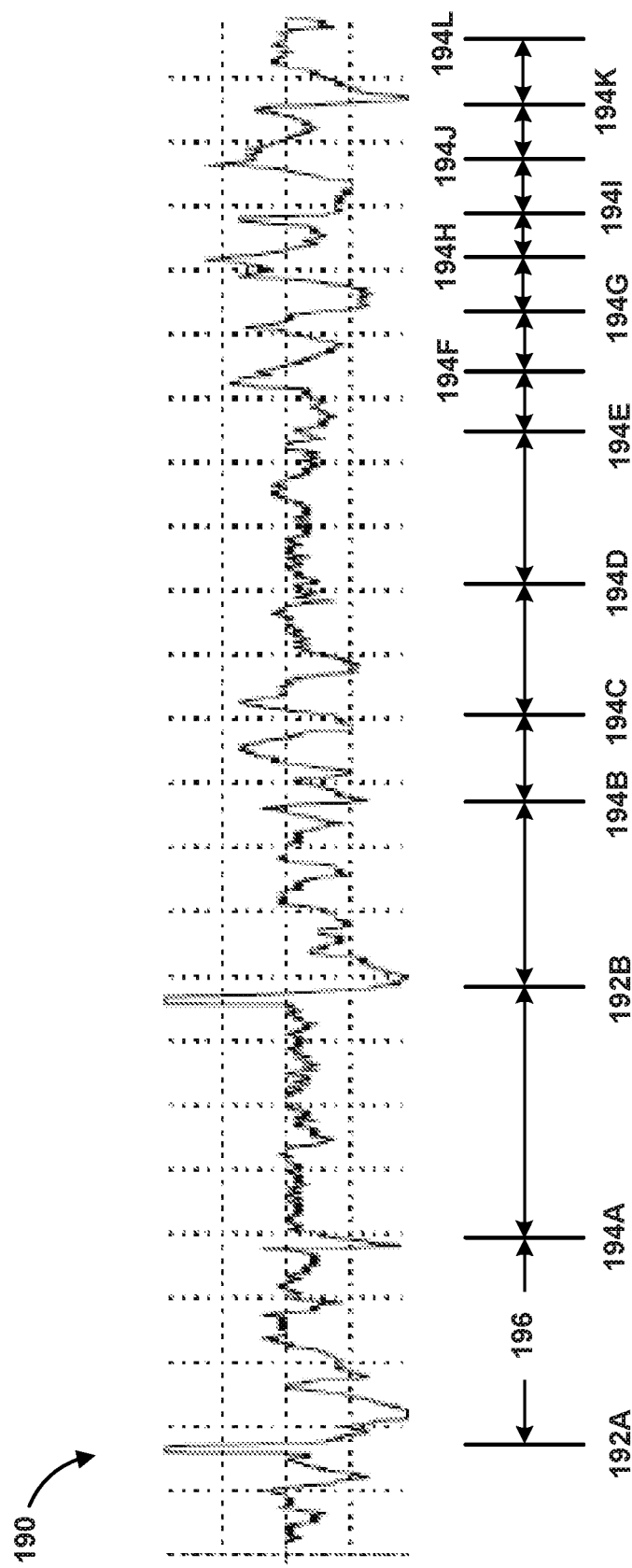
FIG. 5 is a timing diagram illustrating an example cardiac signal sensed via a ventricular lead before and after dislodgement of the ventricular lead.

FIG. 5 is a timing diagram illustrating an example cardiac signal 190, e.g., a ventricular EGM, sensed via a ventricular lead, e.g., ventricular lead 20, when dislodged and during an atrial fibrillation episode. FIG. 5 also illustrates instances at which therapy delivery circuitry 104 of IMD 10 delivered pacing pulses 192A and 192B (collectively "pacing pulses 192") via ventricular lead 20, and instances at which sensing circuitry 102 of IMD 10 detected R-waves 194A-194L (collectively "R-waves 194") in cardiac signal 190. FIG. 5 also illustrates RR intervals 196, only one of which is labeled in FIG. 5 for ease of illustration, determined by processing circuitry described herein, such as processing circuitry 106 of IMD 10. An RR interval is the interval between consecutive ventricular events whether those events are a result of pacing or of intrinsic conduction. In other words, an RR interval may be an interval between consecutive R-waves 194, between consecutive pacing pulses 192, or between a consecutive R-wave 194 and pacing pulse 192, in either order.

Although an atrial EGM is not illustrated in FIG. 5, an atrial fibrillation episode of heart 16 was ongoing during the acquisition of the illustrated ventricular cardiac signal 190. Furthermore, the ventricular lead, e.g., ventricular lead 20, used to acquire ventricular cardiac signal 190 was dislodged during acquisition of cardiac signal 190. Consequently, as illustrated in FIG. 5, cardiac signal 190 demonstrates characteristics associated with dislodgement of ventricular lead 20 during atrial fibrillation.

For example, cardiac signal 190 may be a near-field EGM, and the amplitudes of the features of cardiac signal 190 detected by sensing circuitry 102 as R-waves 194 may be relatively lower and more variable when ventricular lead 20 is dislodged then R-waves detected by sensing circuitry 102 prior to the dislodgment of ventricular lead 20. This is because prior to dislodgement the ventricular depolarizations would only be sensed, while after dislodgement, sensing circuitry 102 may detect as ventricular depolarizations a combination of atrial depolarization and lower amplitude ventricular depolarizations. The features of cardiac signal 190 detected by sensing circuitry 102 as R-waves 194 when ventricular lead 20 is dislodged during atrial fibrillation may include actual ventricular depolarizations, and atrial depolarization or fibrillation signals incorrectly detected as R-waves. The amplitudes of these features may be relatively low due to the electrodes of ventricular lead 20, e.g., tip electrode 22, being in contact with neither of the ventricular or atrial myocardium, and may be variable due to variable proximity of dislodged ventricular lead 20 to ventricular or atrial myocardium during the cardiac cycle. Additionally, the atrial fibrillation signals may generally have lower amplitudes than atrial depolarizations during sinus rhythm.

Processing circuitry 106 (or any other processing circuitry described herein that receives a digitized version of cardiac signal 190 from IMD 10) may determine amplitudes of R-waves 194 detected by sensing circuitry 102 via ventricular lead 20 as a characteristic associated with dislodgement of ventricular lead 20. For example, the processing circuitry may determine the R-wave amplitude to be an absolute value of cardiac signal 190, e.g., near-field ventricular EGM, relative to a baseline at the point of detection of an R-wave 194 or a peak, mean or other amplitude value within a window of cardiac signal 190 around the point of detection of the R-wave.

Processing circuitry 106 may detect dislodgement of ventricular lead 20 based on determined amplitudes of R-waves 194, e.g., detected by sensing circuitry 102 in near-field ventricular EGM via ventricular lead 20, such as based on whether the amplitudes of R-waves 194 are less than an amplitude threshold. The amplitude threshold may be a fixed, predetermined value, or may be a variable value, e.g., determined based on amplitudes of R-waves 194, or cardiac signal 190 generally, when ventricular lead 20 was not dislodged. In some examples, processing circuitry, e.g., processing circuitry 106, determines the amplitude threshold based on the amplitudes of R-waves detected during sinus rhythm or one or more prior induced or spontaneous ventricular fibrillation episodes of patient 14. For example, the amplitude threshold may be a percentage, e.g., 50%, of the amplitudes of R-waves detected during one or more prior induced or spontaneous ventricular fibrillation episodes of patient 14. In one example, the amplitude threshold is 1 mV.

In some examples, processing circuitry 106 detects dislodgement of ventricular lead 20 based on the amplitudes of a threshold percentage or fraction of a group of R-waves 194 that are part of an episode, e.g., a group of R-waves 194 leading up to detection of ventricular fibrillation, being less than the threshold amplitude. In some examples, the group of R-waves 194 includes the R-waves 194 in a detected ventricular fibrillation episode that were associated with RR intervals less than the ventricular fibrillation interval threshold. In one example, the number of R-waves 194 whose amplitude is considered is 18, e.g., the R-waves 194 associated with the 18 RR intervals of 24 consecutive RR intervals below the ventricular fibrillation interval threshold that led to detection of a ventricular fibrillation episode. In one example, processing circuitry 106 detects dislodgement of ventricular lead 20 based on at least 25% of the amplitudes of the group of R-waves 194 being less than the amplitude threshold.

As another example, the variability of the amplitudes of R-waves 194 during dislodgment may be relatively higher than the variability prior to dislodgment of ventricular lead 20. Processing circuitry 106 may detect dislodgement of ventricular 20 based on a measure of the variability of the amplitudes of R-waves 194 exceeding a threshold. In some examples, the measure of variability may comprise a range of the amplitudes. A range of a group of R-wave amplitudes may be a difference between a highest amplitude, or $i^{th}$ highest amplitude, and a lowest amplitude, or $j^{th}$ lowest amplitude, where i and j may be the same or different integers. In some examples, the threshold range may be fixed or variable value, such as a value between 1.0 and 3.0 mV. In some examples, the threshold may be 2.0 mV.

As another example, the variability of RR intervals 196 detected via ventricular lead 20 when the ventricular lead is dislodged may be greater than the variability of RR intervals 196 before dislodgement of ventricular lead 20, e.g., greater than the variability of RR intervals 196 detected via ventricular lead 20 during ventricular fibrillation episodes before dislodgment of ventricular lead 20. Processing circuitry 106 (or any other processing circuitry described herein that receives indications of the timing of pacing pulses 192 and R-waves 194 from IMD 10) may determine one or more parameters indicative of the variability of RR intervals 196 as a characteristic associated with dislodgement of ventricular lead 20 during atrial fibrillation. For example, processing circuitry 106 may determine at least one of a modesum of the RR intervals 196, a ratio of a maximum and a minimum of the RR intervals 196, or an amount of the RR intervals 196 below a threshold length within a group of RR intervals 196 as parameters indicative of the variability of RR intervals 196. The group of RR intervals may be consecutive RR intervals 196, which may have preceded detection of ventricular fibrillation, as described above.

To determine the modesum, in one example, processing circuitry 106 groups interval values into bins, each bin associated with a range of interval values, and determines the percentage of the values of RR intervals 196 that are within the two most populated interval value bins. In one example, processing circuitry 106 detects dislodgment of ventricular lead 20 based on the modesum of the RR intervals 196 being less than the modesum threshold, e.g., 50%. In some examples, the ratio between the maximum and minimum of the RR intervals 196 is a ratio of the maximum to the minimum, and processing circuitry 106 detects dislodgment of ventricular lead 20 based on the ratio exceeding a ratio threshold, e.g., 2.0. In other examples, the ratio between the maximum and minimum of the RR intervals 196 is a ratio of the minimum to the maximum, and processing circuitry 106 detects dislodgment of ventricular lead 20 based on the ratio being less than a ratio threshold.

In some examples, a threshold RR interval length is fixed or variable, and may be based on baseline RR interval lengths 196 prior to an episode. In some examples, the threshold RR interval length is a value between approximately 200 ms and approximately 300 ms, such as approximately 250 ms. In some examples, the threshold amount of RR intervals below the threshold length is a percentage, such as 25%. Processing circuitry 106 may detect dislodgment of ventricular lead 20 based on the percentage (or other amount) of RR intervals less than threshold length being greater than the threshold percentage (or other amount).

In some examples, processing circuitry 106 may determine differences between consecutive RR intervals 196 of the group of RR intervals 196, and may determine a number or percentage of the determined differences that exceed a threshold difference as a parameter indicative of the variability of RR intervals 196. In such examples, processing circuitry 106 detects dislodgment of ventricular lead 20 based on the number or percentage of supra-threshold differences exceeding a threshold number or percentage. In general, processing circuitry 106 may detect dislodgement of ventricular lead 20 based on the variability of RR intervals 196 satisfying a variability threshold, of which the above measures of variability and detection criteria are examples.

In some examples, processing circuitry 106 may detect dislodgement of ventricular lead 20 based on identifying a pattern of RR interval lengths. Such patterns may be particularly evident when a ventricular EGM includes detected R-waves that are both true ventricular depolarizations and atrial depolarizations during sinus rhythm or sinus tachyarrhythmia. The RR interval pattern may include alternating interval lengths, such as an SLSL pattern. Techniques for detecting dislodgment of ventricular leads based on such patterns in near-field and far-field EGMs are described in the '873 publication and '239 publication, respectively. For example, a primary lead dislodgement algorithm may operate during baseline rhythm and a secondary lead dislodgement algorithm may operate during detection of VT or VF. In some examples, the ventricular FF-EGM can be monitored. During the monitoring, the FF-EGM may be checked for an abrupt change in amplitude, an abrupt increase in amplitude variability, or a S-L-S-L sequence of alternating atrial and ventricular EGMs as described above. In other examples, other parameters of the FF-EGM may be monitored, including but not limited to polarity, frequency, content, and morphology. Once lead dislodgement is detected, an algorithm may suspend detection of VF and/or provide immediate notification to the patient and/or remote-monitoring network.

An example of an abrupt change may include determining the median of a measurement over a predetermined time period, such as amplitude, lead impedance, or similar measurement. An abrupt change may be defined as a change in a measurement that increases greater than a threshold amount or decreases greater than a threshold amount, e.g., relative to the median. As one example, an abrupt change in lead impedance may be defined as a change in lead impedance that is more than 75% or less than 60% of the median lead impedance taken over the previous ten days. In another example, an abrupt change in R-wave amplitude may be defined as a decrease of 50% of the median R-wave amplitude over the previous week. In other examples, an abrupt change may include a change in a short-term average, such as over the period of a few hours, when compared to a longer term average for the same measurement, such as over a period of several days.

In some examples, in response to a group of RR intervals 196 satisfying a programmable number of intervals to detect (NID) criterion for detecting ventricular fibrillation (e.g., 18 RR intervals 196 out of 24 consecutive RR intervals 196 being shorter than the ventricular fibrillation threshold), processing circuitry 106 determines the amplitude of R-waves 194 and variability of RR-intervals 196 leading to the satisfaction of the NID criterion, such as consecutive R-waves or RR intervals prior to detection, or the specific RR intervals 196 (e.g., the 18 RR intervals 196) that were shorter than the ventricular fibrillation threshold and R-wave amplitudes associated with those RR intervals.

FIGS. 6-11B are flowcharts illustrating example techniques for identifying dislodgment of a ventricular lead. The flowcharts of FIGS. 6-11B are intended to illustrate the functional operation of IMD 10, medical system 8, and other devices and systems described herein, and should not be construed as reflective of a specific form of software or hardware necessary to practice the methods described. Methods described in conjunction with flow charts presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software modules, which may be executed by themselves or in combination with other software.

The example methods illustrated by FIGS. 6-11B may be performed, by any one or more devices described herein, and may be performed, in part, by processing circuitry of any one or more devices described herein, such as by processing circuitry 106 of IMD 10, processing circuitry 140 of external device 30, processing circuitry 168 of server 164, or processing circuitry of access point 160 and/or computing devices 170. For ease of description, the methods of FIGS. 6-11B will be described hereafter as being performed by processing circuitry 106 of IMD 10.

Figure 6:
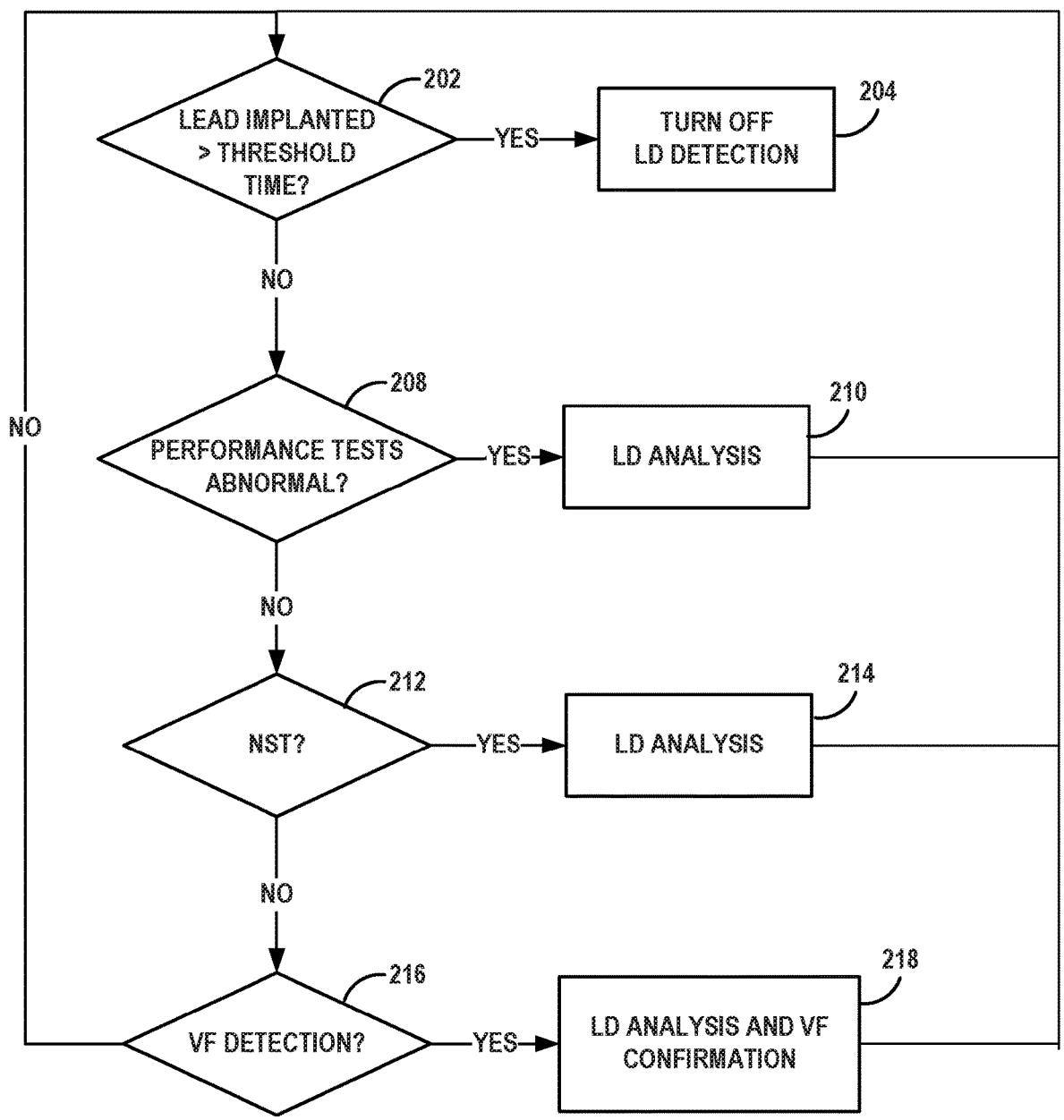
FIG. 6 is a flowchart of an example technique for identifying dislodgment of a ventricular lead.

FIG. 6 is a flowchart of an example technique for identifying dislodgment of a ventricular lead. Additional details will be described in relation to other figures in this disclosure. The steps in the example of FIG. 6, as with other flowchart figures in this disclosure, may be performed in a different sequence than depicted in the example of FIG. 6. In other examples, the techniques of this disclosure may include steps not shown in FIG. 6, or may exclude one or more of the steps shown in FIG. 6.

According to the example of FIG. 6, after a predetermined time period subsequent to implant, e.g., after three, four, or six months, as examples, processing circuitry 106 may disable lead dislodgment surveillance either in response to commands from external device 30 and/or automatically (202). Since the likelihood of lead dislodgement occurring is greatest within the first few months after implanting lead 20, processing circuitry 106 may initiate the lead dislodgement surveillance techniques described herein at the time of implant of ventricular lead 20 in the patient 14. In other words, after ventricular lead 20 has been implanted for a time that exceeds a threshold, processing circuitry 106, for example, may turn off lead dislodgement (LD) detection (204).

IMD 10 may perform a plurality of tests which may include tests to check the integrity of ventricular lead 20 and atrial lead 21, verify pacing thresholds, and other tests to ensure that IMD 10 is functioning properly or to maximize efficiency. For example, testing pacing thresholds may reduce the voltage required to capture the heart 16 of the patient and cause a contraction. Reducing the pacing voltage may increase battery life as well as provided other improved patient outcomes.

One cause of oversensing and resultant inappropriate shocks may include a lead integrity issue such as lead fracture or impending lead fracture. A large number of non-physiologic short RR intervals (NPSRRIs) may indicate that a sensing lead is damaged, such as ventricular lead 20 depicted in FIG. 1. In some examples, an NPSRRI may be less than threshold, which may be 120-140 ms, for example. The R-waves used to determine whether NPSRRIs are present may be sensed using the techniques described herein in the near-field EGM.

A counter may store the cumulative number of NPSRRIs over a period of time, such as since the last programming session for an IMD. As one example, a count that exceeds a threshold, such as more than 30 NPSRRIs in a three-day sliding window period, may be one indicator of a possible lead integrity issue. In some examples according to the techniques of this disclosure, a count that exceeds the threshold may also indicate possible lead dislodgement. In some examples, processing circuitry 106 may perform further lead dislodgement analysis in response to the NPSRRI count exceeding a threshold. Determining, periodically or otherwise, whether a NPSRRI count exceeds a threshold, or other evaluation of NPSRRIs, may be considered a determination of whether a performance test was abnormal (208).

In some examples, the counter may be referred to as a sensing integrity counter (SIC). In some examples, the SIC may be reset during a programming session, such as during a patient's follow-up visit. In other examples, the SIC may be reset remotely, such as via access point 160, depicted in FIG. 4. In some examples, the SIC may reset under other conditions, or may not be reset. The abnormal NPSRRI is different than the abnormal SLSL pattern described above in relation to FIG. 5 and below in relation to step 266 of FIG. 7.

Some examples of performance tests are conducted periodically. For example, processing circuitry 106 may perform a lead impedance test several times per day and a pacing threshold test once a day or once every few days. In some cases, abnormal performance tests may indicate a possible lead dislodgement. In the example of FIG. 6, when processing circuitry 106 detects an abnormal performance test (YES of 208), processing circuitry 106 may initiate further lead dislodgement (LD) analysis (210). Example details of further LD analysis (210) will be described below in relation to FIG. 7.

Although primarily described as indicative of lead or system integrity, performance tests may also include any physiological measurement. For example, a pacing threshold may be considered a physiological measurement, because a pacing threshold measures a physiological function, i.e., the response of cardiac tissue to electrical stimulation. Other examples of physiological measurements may include RWA, PWA, and RR intervals.

Within the LD detection period (NO of 202), when processing circuitry detects a non-sustained tachycardia (NST) episode (YES of 212), processing circuitry 106 may also initiate additional LD analysis (214). In some examples, processing circuitry 106 may detect an NST based on interval criteria, such as an average duration of R-R intervals is less than a threshold, such as less than 220 milliseconds (ms). In other examples, processing circuitry 106 may additionally or alternatively detect an NST based on other cardiac intervals, e.g., P-P, P-R or R-P intervals, or other aspects, e.g., morphology, of the cardiac electrical signal.

In the example of an NST episode, processing circuitry 106 may store an EGM of the NST episode in memory 108. Processing circuitry 106 may use the stored EGM to perform the additional LD analysis (214). Example details of the additional LD analysis (214) performed in response to detecting an NST episode will be described in more detail in relation to FIG. 8 below.

In some examples of ventricular lead 20 dislodgement, IMD 10 may interpret other cardiac signals as ventricular fibrillation (VF). For example, if the lead dislodgement generates noise on the electrodes of ventricular lead 20, IMD 10 may inappropriately interpret the noisy cardiac signals as VF. Similarly, if ventricular lead 20 moves out of the RV apex and the electrodes, such as electrodes 24 and 22, move into the right atria (RA), IMD 10 may interpret RA cardiac signals as RV cardiac signals. In the example of atrial fibrillation (AF), a dislodged ventricular lead 20 may inappropriately cause processing circuitry 106 of IMD 10 to interpret the AF as VF. In the example of FIG. 6, during the LD detection period (202), processing circuitry 106 may detect VF (YES of 216) and initiate LD analysis and VF confirmation (218) to prevent inappropriate therapy delivery, as described above. Example details of the additional LD analysis and VF confirmation (218) performed in response to detecting VF will be described in more detail in relation to FIG. 9 below. Processing circuitry 106 may continue to monitor (NO of 216) for abnormal performance tests (208), NSTs (212), and VF detection (218) during the LD detection period (NO of 202).

Although FIG. 6 illustrates an example in which lead dislodgment analysis is performed in response to certain condition, the techniques described herein are not so limited. In some examples, lead dislodgement analysis may be performed in response to other events, such as other system integrity or physiological events, periodically, or in response to a user command.

Figure 7:
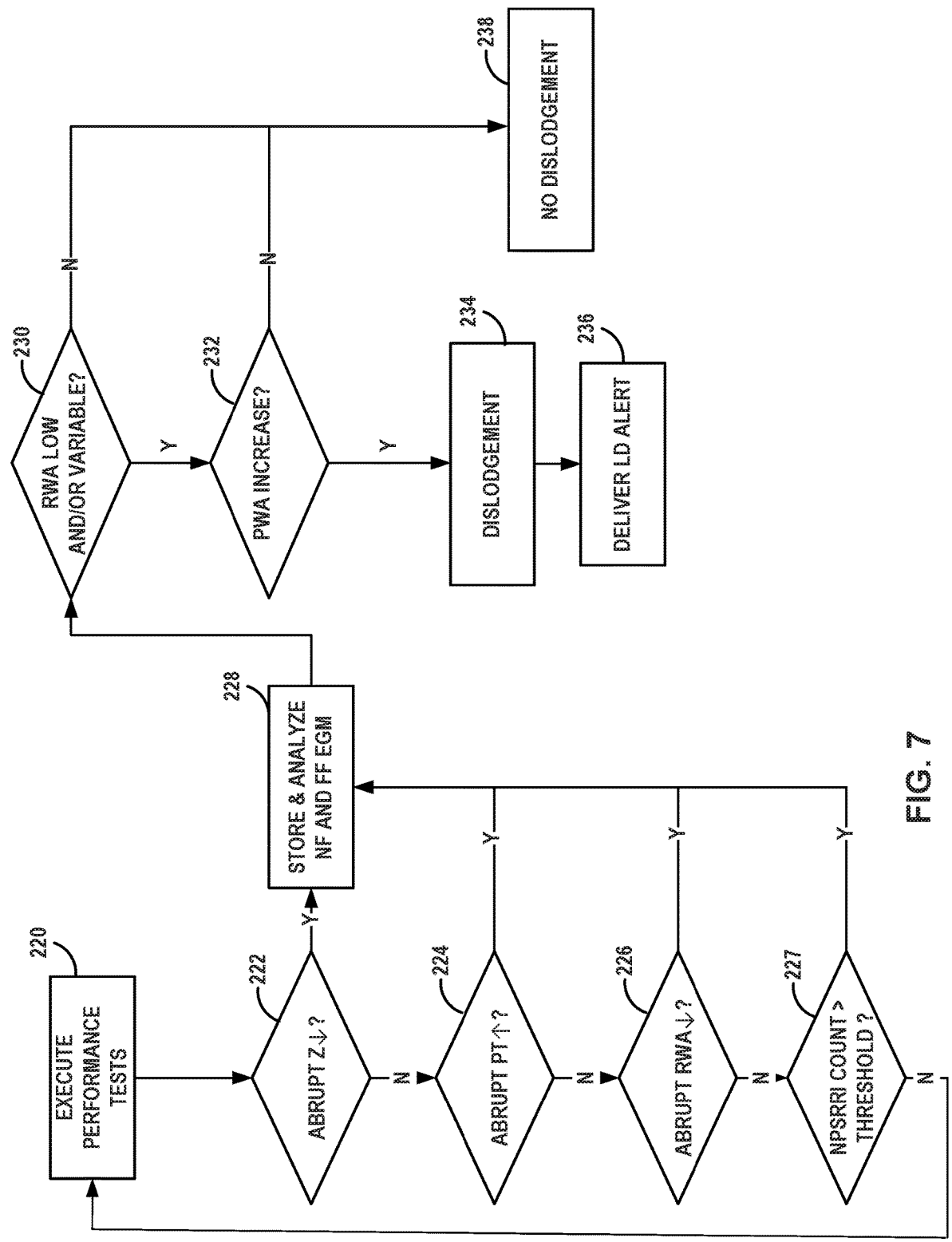
FIG. 7 is a flowchart of an example technique for identifying dislodgment of a ventricular lead in response to abnormal lead performance tests.

FIG. 7 is a flowchart of an example technique for identifying dislodgment of a ventricular lead in response to abnormal lead performance tests. In the example of FIG. 7, processing circuitry 106 executes performance tests (220), which may include testing the impedance of one or more vectors including the electrodes on ventricular lead 20, testing a capture threshold for pacing delivered via lead 20, testing the amplitude of R-waves detected or other aspects of the EGM sensed via one or more electrodes of ventricular lead 20, or evaluating a count of NPSRRIs on an SIC. The performance tests may be performed periodically, or in response to a user-command or other process indicating such tests are desired. Any one or more of performance tests 222-227 meeting a threshold, as described, may trigger processing circuitry 106 to store and analyze EGMs in step 228. Also, though the example of FIG. 7 includes performance tests 222-227, in other examples, other performance tests, or other comparisons may also or alternatively be included, or the analysis of EGMs may be performed periodically or in response to a user command. Further, although the example of FIG. 7 indicates that EGMs are stored and analyzed in response to the performance test, one or both of the storage or analysis may have occurred, at least in part, before or during the performance test, e.g., in the case where processing circuitry 106 stores a rolling window of EGM data.

Processing circuitry 106 may execute a lead impedance test of the impedance of one or more vectors provided by ventricular lead 20. Lead impedance may change gradually over time as the heart tissue grows around the lead after implantation. However, an abrupt decrease may indicate the ventricular lead has come free from the apex of heart 16 (222). If the abrupt lead impedance decrease satisfies a threshold (YES of 222), processing circuitry 106 may store and analyze a near-field EGM and a far-field EGM sensed via ventricular lead 20 to determine whether dislodgment of ventricular lead 20 is detected (228). In one example, an abrupt decrease in lead impedance may be defined as a lead impedance measurement less than 75% of the median of the most recent X measurements or a decrease of more than 100Ω. This is just one example of a possible threshold for abrupt lead impedance change.

If the electrodes of the ventricular lead 20, e.g., electrodes 22 and 24 no longer are in contact with the heart tissue, this can cause an increase in pacing threshold. Pacing thresholds can change gradually with blood sugar levels, patient health and other factors. But a sudden change in pacing threshold may indicate a lead dislodgement. An example of an abrupt pacing threshold change (224) may include a threshold change>2.0×median of last 7 days or, for example, a threshold that exceeds 2.0 V. If the abrupt pacing threshold increase satisfies a threshold (YES of 224), processing circuitry 106 may store and analyze a near-field EGM and a far-field EGM sensed via ventricular lead 20 to determine whether dislodgment of ventricular lead 20 is detected (228). In some examples, the pacing threshold test may be conducted as a pacing threshold check, as described below in relation to step 304 of FIG. 10.

R-wave amplitude (RWA) may change gradually over time, similar to lead impedance. However, an abrupt decrease in RWA (226) may indicate ventricular lead 20 has dislodged and moved away from the heart tissue in the apex of heart 16. In some examples, the lead may move into the atrium and ventricular lead 20 may begin sensing atrial depolarizations, which may have a significantly lower amplitude than a ventricular depolarization. An example of an abrupt RWA decrease may include an RWA that is either less than 0.5× the median of last seven days (or some other number of previous periodic measurements) or an RWA decrease greater than a fixed threshold, such as a decrease of more than 2.0 mV. If the abrupt RWA decrease satisfies a threshold (YES of 226), processing circuitry 106 may store and analyze a near-field EGM and a far-field EGM sensed via ventricular lead 20 to determine whether dislodgment of ventricular lead 20 is detected (228). Sensing circuitry 102 may sense the near-field EGM via electrodes 22 and 24 of ventricular lead 20, and the far-field EGM via electrode 42 of ventricular lead 20 and housing electrode 12, in one example.

According to the example of FIG. 7, processing circuitry 106 determines an amplitude of one or more of R-waves 194, e.g., as described with respect to FIG. 5, in both the near-field EGM and the far-field EGM (228). In some examples, processing circuitry 106 determines the R-wave amplitudes in the stored near-field and far-field EGMs by determining values of the digitized EGMs (e.g., differences between maximum and minimum signal values) within windows around points identified as an R-wave through application of conventional R-wave identification techniques (e.g., as described above with respect to FIG. 2) to one of the EGMs (e.g., the near-field EGM).

In examples of ventricular lead 20 dislodgement, the RWA may decrease and RWA variability may increase, for the reasons discussed above. According to the example technique of FIG. 7, processing circuitry 106 may determine whether the RWA in one or both of the near-field and far-field EGM is low and/or variable (230). Processing circuitry 106 may compare the RWA metrics to a threshold. For example, processing circuitry 106 may determine whether an amplitude of a threshold percentage (e.g., 25%) of a group of R-waves 194 is less than an amplitude threshold (e.g., 1 mV). In other words, if at least 25% of the RWA of a group of R-waves as shown in the stored EGM is less than a threshold, processing circuitry 106 may determine that ventricular lead 20 has dislodged. The thresholds for determining lead dislodgement may be different for the far-field RWA metrics as compared to the threshold for the near-field RWA metrics.

Processing circuitry 106 may also measure the variability of the RWA for one or both of the near-field and far-field EGM. In some examples, far field RWA variability may be greater than near-field RWA variability when a ventricular lead dislodges to the atrium. As one example, if the range of the RWA measurements for a group of R-waves exceeds a threshold, such as the range exceeds 2.0 mV, processing circuitry 106 may determine that ventricular lead 20 has dislodged. The group of R-waves may be a certain number of R-waves, such as twenty R-waves, or may be over a period of time, such as over a ten second interval. In other words, if the difference between the maximum RWA and the minimum RWA in a group of R-waves satisfies a threshold, processing circuitry 106 may determine ventricular lead 20 dislodgement. In some examples, processing circuity 106 may determine dislodgement of ventricular lead 20 if only the RWA variability exceeds a threshold. In other examples both the RWA must satisfy a RWA threshold and the RWA variability must also satisfy a threshold before determining lead dislodgement. Processing circuitry 106 may consider any combination of RWA metrics to determine lead dislodgement. Furthermore, in some examples, processing circuitry 106 may require the RWA and/or RWA variability metrics to exceed the thresholds in both the near-field and the far-field EGMs for an indication of dislodgment, or only in one of the near-field and the far-field EGMs for an indication of dislodgment.

If the RWA condition for indicating lead dislodgement is satisfied (YES of 230), processing circuitry 106 may determine whether P-wave amplitudes in one or both of the near-field or far-field EGMs have increased (232). Note that in the example of actual VF, processing circuitry may not be able to measure P-wave amplitude. If a ventricular lead, such as ventricular lead 20 dislodges toward the atrium, the lead may measure a P-wave amplitude increase as an indicator of inappropriate VF. The techniques of this disclosure may determine lead dislodgement with a single chamber device using only ventricular lead 20. Processing circuitry 106 may determine the location of a P-wave in the NF-EGM and FF-EGM with techniques as described above, such as measuring an amplitude of an EGM at the expected time before an R-wave where a P-wave should occur. In the example of a dual chamber device, processing circuitry 106 may compare the P-wave as measured on the atrial EGM to both determine the location of the P-wave on the ventricular EGMs, and compare any measured P-wave amplitude increase in the ventricular EGMs with the P-wave amplitude on the atrial EGM. For example, an apparent P-wave amplitude increase on the ventricular far-field EGM with no increase on the atrial EGM, may be an indicator of ventricular lead dislodgement. U.S. Patent Publication No. 2016/0235992 by Sarkar (hereinafter "the '992 publication"), which is incorporated herein by reference in its entirety, includes examples of techniques that may be used for determining P-wave amplitudes from an electrode vector other than a near-field atrial vector, such as from a far-field ventricular EGM.

Processing circuitry 106 may determine that P-wave amplitudes have increased based on a mean or median of amplitudes being greater than a threshold determined based on a non-dislodgment baseline, or based on an amount of P-waves having amplitudes exceeding the threshold value. In some examples, the P-wave amplitude is determined by far field P-wave measurement. The threshold may be a fixed value above the baseline or a percent increase over the baseline, for example. In some examples IMD 10 may take an initial P-wave baseline after implant either automatically, e.g., after a first normal lead impedance measurement, or by command from external device 30. IMD 10 may periodically take additional P-wave baseline measurements, such as during follow up health care visits by patient 14, or automatically according to a schedule or when triggered by events, such during as other lead performance tests. The P-wave amplitude baseline value may be determined and or updated based on such P-wave measurements, e.g., based on a mean or median of such measurements, or a recent grouping thereof. The example of FIG. 7 depicts the PWA measurement as only following a confirmed determination of low RWA and/or RWA variability in one or both of the EGMs (230). However, in other examples steps 230 and 232 may occur in any order and may be independent of each other. In other examples, processing circuitry 106 may not perform step 232 and, in the example of FIG. 7 after YES of 230 continue directly to step 234.

In some examples, the P-wave amplitude measurement to confirm lead dislodgment may only be applied during sinus rhythm or during a sinus tachyarrhythmia episode. During AF the P-waves may be distorted and more difficult to measure. P-waves may be more defined during sinus rhythm.

In examples where electrodes, such as coil electrode 42, move into the atria, the far-field EGM may show an increase in PWA. Therefore, an increase in PWA, particularly in a far-field EGM, may indicate lead dislodgement of ventricular lead 20. In some examples, processing circuitry 106 detects P-waves in a far-field EGM, e.g., using techniques described in commonly-assigned U.S. Pat. No. 9,486,155 B2 (hereinafter "the '155 patent"), incorporated herein by reference in its entirety. As described in the '155 patent, IMD 10 may detect a P-wave of a cardiac signal by determining a P-wave sensing window within the cardiac signal, e.g., based on timing relative to an R-wave occurring before or after the P-wave. IMD 10 may compare signal characteristics of the cardiac signal within portions of the P-wave sensing window to other portions of the P-wave sensing window, or to a P-wave template, to identify a P-wave. In some examples, once the P-wave has been sensed, e.g., using the techniques of the '155 patent, processing circuitry 106 may measure the amplitude of the P-wave by determining a difference between a maximum voltage and a minimum voltage of the EGM within a window including the detected P-wave. The amount of PWA increase may depend on the location of the electrode in ventricular lead 20 for which sensing circuitry 102 is configured to measure PWA.

In the example of FIG. 7, processing circuitry 106 detects dislodgement of ventricular lead 20 (234) based on the RWA condition being satisfied (YES of 230) and confirmed by a PWA increase satisfying a threshold (232). Processing circuitry 106 may not detect dislodgement (238) of ventricular lead 20 if either the RWA and/or RWA variability, or the PWA increase do not meet their respective thresholds (NO of 232 and 230). In examples where processing circuitry 106 detects a lead dislodgement (234), processing circuitry 106 may trigger a lead dislodgement (LD) alert (236) as described above.

In some examples, in addition to or instead of detecting dislodgment of ventricular lead 20 based on identifying an increase in amplitude of P-waves in one or more of the EGMs, processing circuitry may detect dislodgment of ventricular lead 20 based on one or more other PWA metrics, such as the variability of the P-wave amplitudes. A relatively high P-wave amplitude variability may indicate a dislodgement of the ventricular lead. Any of the variability measurements described above with respect to R-wave amplitudes may be used to measure the variability of P-wave amplitudes, including a range (e.g., maximum-minimum) over a period greater than a threshold, or a modesum less than a threshold.

Figure 8:
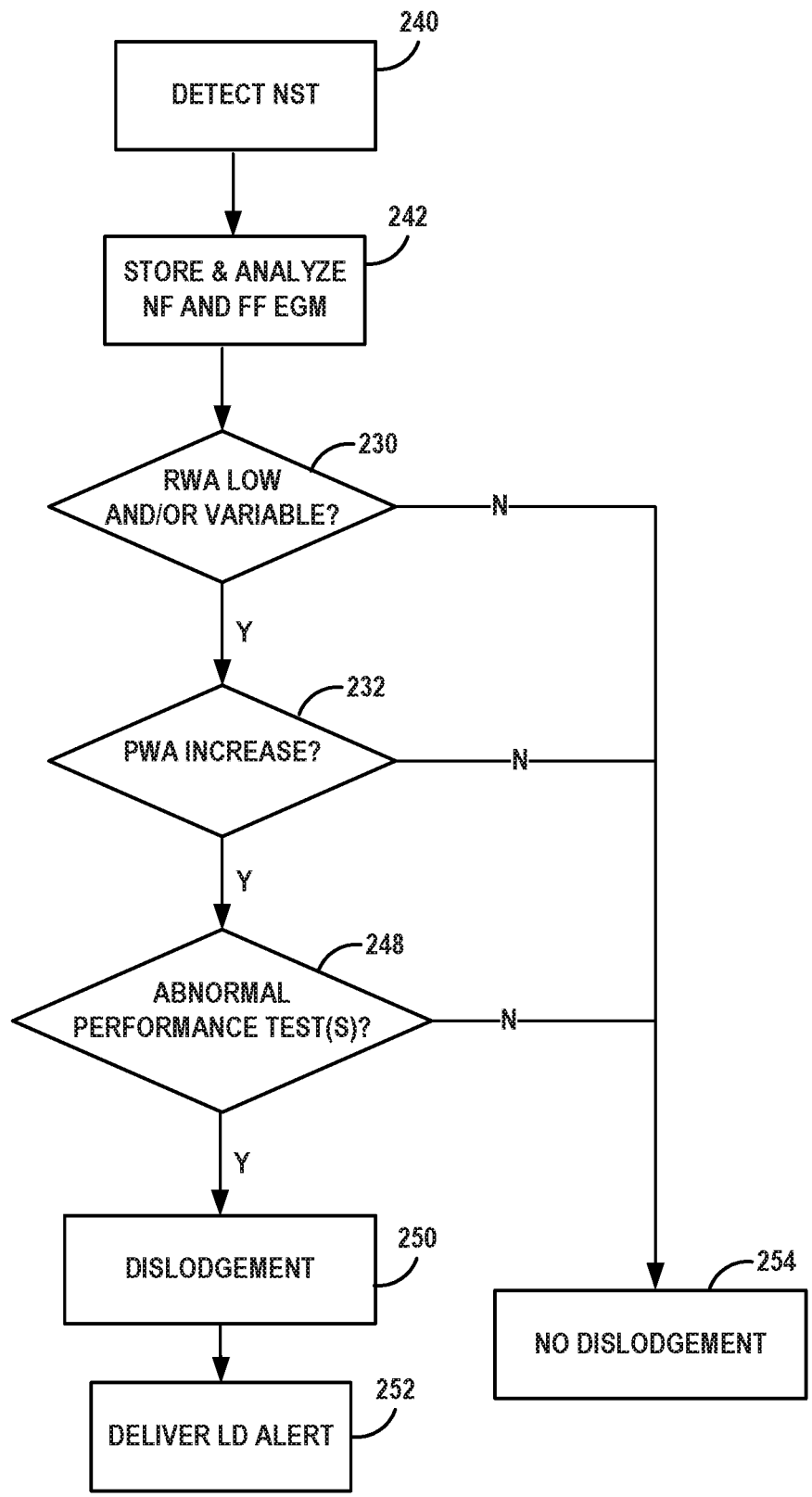
FIG. 8 is a flowchart of an example technique for identifying dislodgment of a ventricular lead in response to detection of a non-sustained tachyarrhythmia.

FIG. 8 is a flowchart of an example technique for identifying dislodgment of a ventricular lead in response to detection of a non-sustained tachyarrhythmia. As described above in relation to FIG. 6, IMD 10 may detect a NST event (240). Processing circuity 106 may automatically record and store both a near-field EGM and a far-field EGM of the NST event, in some examples (242). Within the LD dislodgement period, as described for step 202 of FIG. 6, processing circuity 106 may also conduct a lead dislodgement analysis after an NST event. As described above, processing circuitry 106 may determine a near-field value of one or more R-wave amplitude metrics based on amplitudes of R-waves identified in the near-field EGM and a far-field value of the one or more R-wave amplitude metrics based on amplitudes of R-waves identified in the far-field EGM. The R-wave metrics may include RWA and RWA variability as described above (230). Processing circuitry 106 may determine that RWA and/or RWA variability satisfy a threshold in one or both of the near-field EGM and the far-field EGM, and confirm a possible lead dislodgement by checking for a PWA increase (232), such as in the far-field EGM, as described above with reference to FIG. 7.

The example of FIG. 8 depicts that after both the PWA increase (232) and the RWA and/or RWA variability (230) satisfy a threshold, processing circuitry 106 may execute unscheduled performance tests (248), such as checking for decreased lead impedance (222 of FIG. 7), increased pacing threshold (224 of FIG. 7), and/or decreased R-wave amplitude (226 of FIG. 7). The order of steps 230, 232 and 248 are one example, and in other examples steps 230, 232, and 248 may occur in any order and may also be independent of each other. Some example methods may exclude one or more of the steps 230, 232, and 248, and/or include additional steps. For example, processing circuity 106 may not include a lead impedance check (222 of FIG. 7) as part of executing the performance tests.

As depicted by FIG. 8, processing circuitry 106 may detect dislodgement of ventricular lead 20 (234) based on the RWA and/or RWA variability meeting their respective thresholds in one or both of the EGMs (YES of 230) and confirmed by a PWA increase satisfying a threshold in one or both of the EGMs (YES of 232), and further confirmed by one or more abnormal performance tests (YES of 248). In examples where processing circuitry 106 detects a lead dislodgement (234), processing circuitry 106 may trigger a lead dislodgement (LD) alert (236) as described above. Processing circuitry 106 may not detect dislodgement (254) of ventricular lead 20 if any of the performance tests (248), the RWA and/or RWA variability (230), or the PWA increase (232) conditions are not satisfied.

Figure 9:
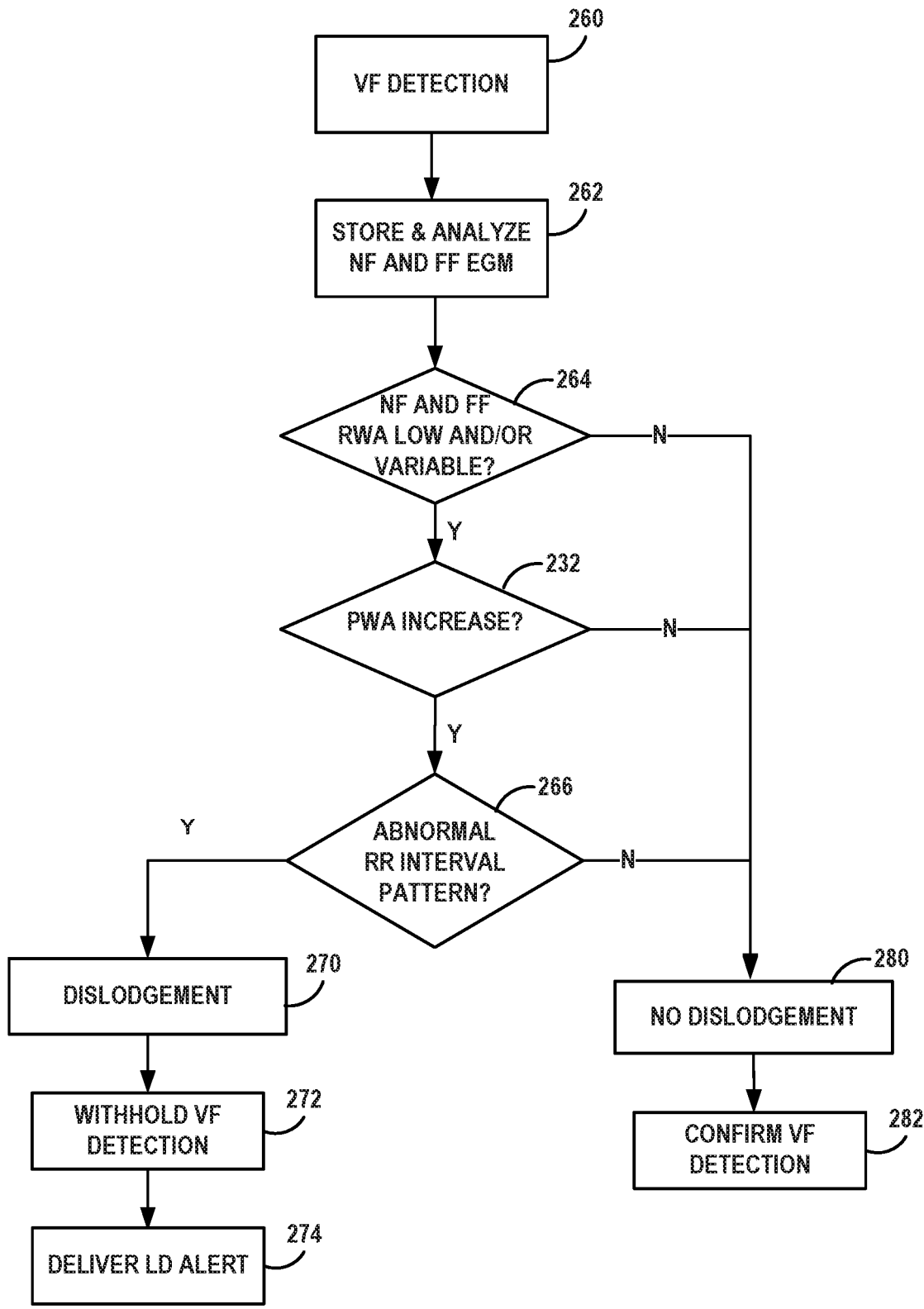
FIG. 9 is a flowchart of an example technique for detecting dislodgment of a ventricular lead and determining whether to withhold or confirm ventricular fibrillation detection.

FIG. 9 is a flowchart of an example technique for detecting dislodgment of a ventricular lead and determining whether to withhold or confirm ventricular fibrillation (VF) detection (260). Processing circuitry 106 may employ any technique for detecting ventricular fibrillation, e.g., based on the length of a number of RR intervals in an episode being less than a threshold length and/or other parameters, including signal morphology. As described in FIG. 6, processing circuitry 106 may execute lead dislodgement analysis to confirm VF detection and to avoid inappropriate therapy delivery (218 of FIG. 6) in response to detecting VF (YES of 216). Processing circuitry may automatically record and store both a far-field EGM and near-field EGM associated with a VF episode (262).

Processing circuitry 106 may analyze the stored EGM for R-wave amplitude metrics, including RWA and RWA variability, in both near-field and far-field, as described above for step 230 in FIG. 7. In some examples, e.g., for detection of lead dislodgment in response to abnormal performance tests and/or detection of an NST, processing circuitry 106 may consider the condition of a relatively low and/or variable RWA (230 in FIGS. 7 and 8) to be satisfied if the RWA is relatively low or variable (or low and variable) in one of the EGMs. In some examples, e.g., for detection of lead dislodgment and confirmation of ventricular fibrillation detection in response to detection of ventricular fibrillation, processing circuitry 106 may require greater satisfaction of the RWA conditions, such as R-wave amplitudes being both low and variable, and/or one or both of low amplitude and variability in both the near-field EGM and the far-field EGM. In the example of FIG. 9, processing circuitry 106 determines whether RWA is low and/or variable in both the near-field EGM and the far-field EGM (264).

In the illustrated example, FIG. 9 depicts processing circuitry 106 as confirming a determination that RWA and/or RWA variability satisfy a threshold in both EGMs (YES of 264) by determining whether a PWA increase satisfies a threshold (232), e.g., as described above with respect to FIGS. 7 and 8, and further determining whether the RR interval pattern is abnormal in one or both of the EGMs (266). As described above, processing circuitry 106 may identify abnormal RR interval patterns based on relatively high RR interval length variability, or an abnormal pattern of RR interval lengths, such as an SLSL pattern. Example techniques for identifying abnormal RR interval patterns in near-field EGMs are described in the '873 publication and commonly-assigned U.S. Patent Publication No. 2017/0274204 by Gunderson (hereinafter "the '204 publication"), which is incorporated herein by reference. Example techniques for identifying abnormal RR interval patterns in far-field EGMs are described in the above-incorporated '239 publication.

As described above, the P-wave amplitude measurement may only apply during sinus rhythm or during a sinus tachyarrhythmia episode. During AF the P-waves may be distorted and more difficult to measure. P-waves may be more defined during sinus rhythm. In some examples, (not shown in FIG. 9), if the variability in the RR intervals and SLSL pattern satisfies criteria for a sustained tachyarrhythmia episode, e.g., variability greater than a first threshold but less than a second threshold, processing circuitry 106 may execute the PWA test described in step 232. If the RR variability component indicates very irregular RR internals, e.g., greater than the second variability threshold, which may indicate AF, then processing circuitry 106 may bypass the P-wave amplitude check (232). In other words, in other examples, processing circuitry 106 may not perform step 232 and, in the example of FIG. 9 after YES of 264 continue directly to step 266. In other examples, the steps of FIG. 9 may be in a different order, for example step 266 may be executed before step 232.

In some examples, processing circuitry 106 may determine a variability of one or both of the EGMs as described with respect to FIG. 5. Processing circuitry 106 may determine whether a modesum of consecutive RR intervals 196 is less than a modesum threshold (e.g., 50%) and/or a ratio of the maximum to the minimum of the consecutive RR intervals is greater than the ratio threshold (e.g., 2.0). In some examples, such as during AF, a dislodged ventricular lead may include both atrial and ventricular components with varying amplitudes. The AF signal may be low amplitude because the ventricular lead is not fixed in the atrium and the ventricular signal may be small and varying because the lead has dislodged from the ventricle. In some examples a percentage of beats with low amplitude (e.g. >25% with <1 mV amplitude) along with the modesum and maximum to minimum RR intervals criteria above may indicate lead dislodgement, as described in commonly-assigned U.S. Patent Publication No. 2017/0274204 by Gunderson, which is incorporated herein by reference in its entirety.

In response to determining an abnormal RR interval pattern (YES of 266), processing circuitry 106 may determine ventricular lead 20 has been dislodged (270). In some examples, processing circuitry 106 may withhold VF detection (272). In other examples, processing circuitry 106 may detect VF, e.g. may record a VF episode in memory 80, but withhold delivery of antitachyarrhythmia therapy, such as an antitachyarrhythmia shock. Also, in some examples, processing circuitry 106 may deliver a lead dislodgement alert (274), as described above, for example in relation to FIG. 1.

In response to determining there is no abnormal RR interval pattern (NO of 266), processing circuitry 106 may determine ventricular lead 20 no dislodgement of ventricular lead 20 (280). In some examples processing circuitry 106 may confirm VF detection (282).

Figure 10:
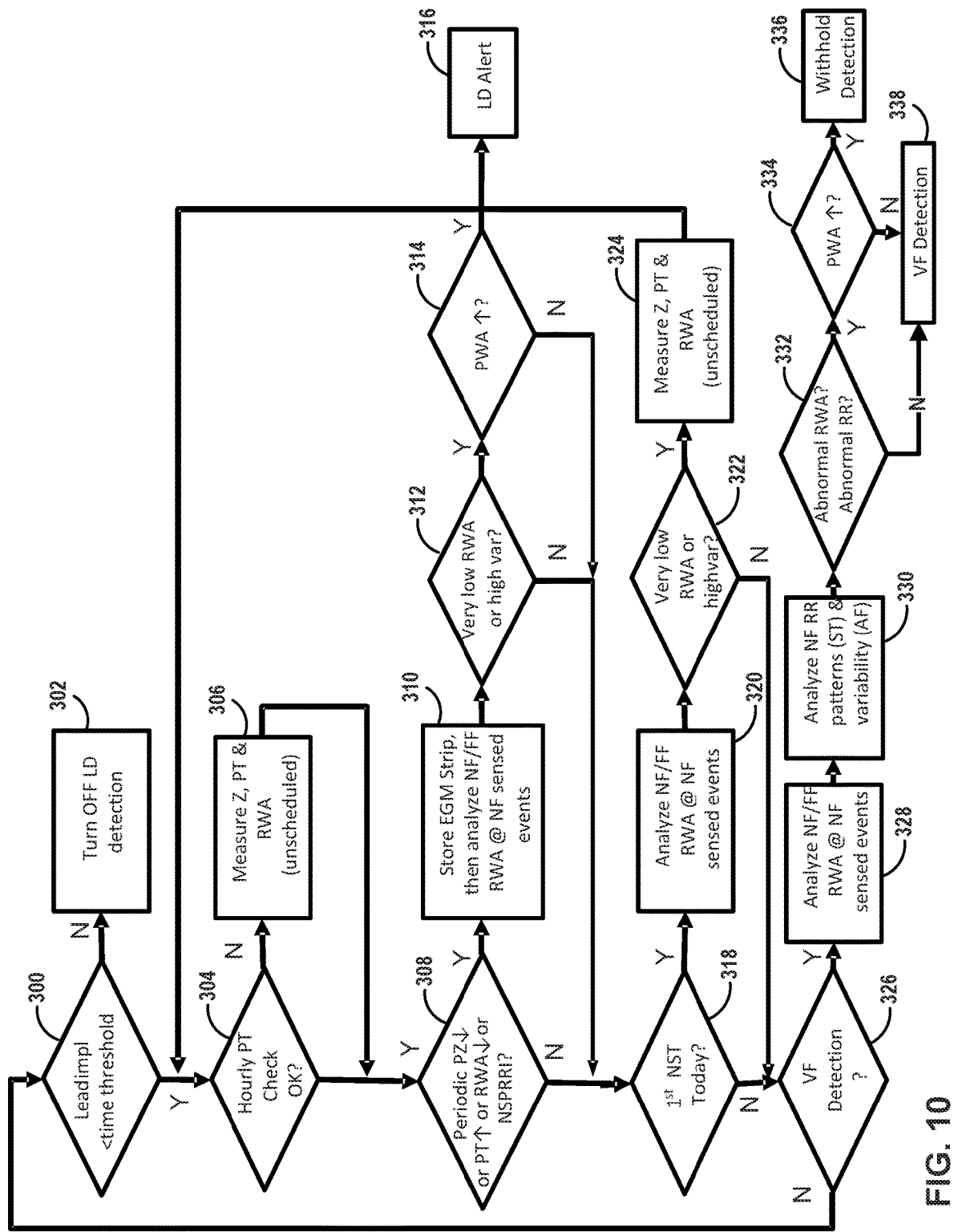
FIG. 10 is a flowchart of another example technique for identifying dislodgment of a ventricular lead.

FIG. 10 is a flowchart of another example technique for identifying dislodgment of a ventricular lead. FIG. 10 includes features that may correspond to the features described above for FIGS. 6-9, and may provide an overview of an example operation of processing circuitry of a medical device system, such as processing circuitry 106 used as the example in FIG. 10, to determine lead dislodgement.

According to the example of FIG. 10, processing circuitry 106 determines whether the time since implant of ventricular lead 20 is less than a threshold (300). When the time since implant exceeds the threshold (NO of 300), processing circuitry 106 may turn off lead dislodgment (LD) detection (302).

During the LD detection period (YES of 300), processing circuitry 106 checks the pacing threshold for ventricular lead 20 hourly, or at some other period (304). The periodic pacing threshold check may include a small reduction in pacing amplitude from the current pacing threshold to determine whether the current pacing threshold provides an appropriate safety margin for ensuring consistent capture. In some examples, a pacing threshold check may include a pacing confirmation at a specific pacing voltage to confirm pacing capture at that voltage. In some examples, a pacing threshold check used for determining whether to further analyze the EGMs to identify lead dislodgment may check the pacing threshold at a predetermined voltage, such as 2.5 V or 5 V, regardless of the current pacing threshold setting of the IMD. In some examples, processing circuitry 106 may check the pacing threshold at a first predetermined voltage. If there is no capture, processing circuitry 106 may check the pacing threshold at a second predetermined voltage. For example, processing circuitry may check the pacing threshold at a single value of 2.5 V, then check the pacing threshold at a second single value of 5.0V if there is no capture.

Processing circuitry 106 may determine that the pacing threshold check passed if the pacing check at the predetermined voltages results in pacing capture. A pacing threshold check at one predetermined value may be enough to determined that the pacing threshold is not abnormal, especially in examples where a lead is implanted for a short period of time, e.g. a few months. A pacing threshold check may also be referred to as a capture verification or pacing capture verification.

A pacing threshold check may determine whether or not the pacing threshold is too high. In some examples, the frequency of a pacing threshold check or capture verification may depend on the time since implant. For example, within the first month of implant, processing circuitry 106 may schedule a pacing threshold check every four hours, because the risk of lead dislodgement may be higher shortly after implant and before the heart tissue grows around the lead electrode to hold the lead in place. Over the next three-month interval, processing circuitry 106 may schedule a pacing threshold check less frequently, such as every eight or twelve hours.

In response to failure of the test pulses at the reduced amplitude to capture the heart (NO of 304), processing circuitry 106 may make unscheduled tests of the performance of ventricular lead 20, such as of the impedance, pacing threshold, and R-wave amplitude, as described herein (306). The performance test for pacing amplitude may include a more complete test of amplitudes to identify a new pacing threshold for subsequent use, e.g., test a series of decreasing or increasing voltage pacing pulses to determine the minimum pacing threshold for capture. A pacing threshold check, e.g., at a single predetermined value, may have an advantage over a full pacing threshold analysis in reduced consumption of battery capacity. A full pacing threshold analysis may pace numerous times at a plurality of voltages to determine the specific pacing threshold. A pacing threshold check may include a single pacing output or only a few pacing outputs, thereby reducing the battery consumption. For example, a pacing threshold check may include a pace pulse at a first amplitude, such as 2.5V amplitude. If the first amplitude does not capture, the pacing threshold check may pace at a second amplitude, such as 5 V. In response to both amplitudes failing to capture, the processing circuitry 106 may determine that the pacing threshold check failed, and take other steps, as depicted for example in FIG. 10.

Steps 308-316 of FIG. 10 may generally correspond to the functions illustrated and described with respect to FIG. 7. Processing circuitry 106 executes performance tests (308), which may include testing the impedance of one or more vectors including the electrodes on ventricular lead 20, testing a capture threshold for pacing delivered via lead 20, testing the amplitude of R-waves detected or other aspects of the EGM sensed via one or more electrodes of ventricular lead 20, or evaluating a count of NPSRRIs to a threshold. The performance tests may be performed periodically, or in response to a user-command or other process indicating such tests are desired. Any one or more of performance tests meeting a threshold, such as 222-227 of FIG. 7, may trigger processing circuitry 106 to store and analyze EGMs in step 310. Performance tests may include an abrupt decrease in periodic lead impedance (PZ ↓), an abrupt increase in pacing threshold (PT ↑), a decrease in R-wave amplitude (RWA ↓) and the NPSRRI count exceeding a threshold. In other examples, other performance tests or other comparisons may also or alternatively be included, or the analysis of EGMs may be performed periodically or in response to a user command.

As described above in relation to 228 of FIG. 7, if the periodic or triggered performance tests meet a predetermined threshold (YES of 308), processing circuitry 106 may store and analyze a near-field EGM and a far-field EGM sensed via ventricular lead 20 to determine whether dislodgment of ventricular lead 20 is detected (310). Analysis of the EGMs may include determining whether the RWA in one or both of the near-field and far-field EGM is low and/or variable (312). In some examples, processing circuitry 106 may compare the RWA metrics to a threshold as described above in relation to 230 of FIG. 7. In response to processing circuitry 106 determining that the RWA is not low or variable (NO of 312), processing circuitry may continue with other tests.

In response to processing circuity 106 determining that the RWA is low or variable (YES of 312), processing circuitry 106 may determine whether P-wave amplitudes in one or both of the near-field or far-field EGMs have increased (314). For example, an apparent P-wave amplitude increase on the ventricular far-field EGM with no increase on the atrial EGM, may be an indicator of ventricular lead dislodgement. In examples where processing circuitry 106 detects a P-wave amplitude increase (PWA ↑), processing circuitry 106 may trigger a lead dislodgement (LD) alert (316) as described above in relation to FIG. 1. In some examples, as described above in relation to 232 of FIGS. 7-9, processing circuitry 106 may not perform step 232 and, in the example of FIG. 10 after YES of 312 continue directly to step 316.

Steps 318-324 may generally correspond to steps 240, 242, 230, 232, and 248 described above with respect to FIG. 8. In some examples, the technique of FIG. 8 may be performed in response to the first (or other ordinal number) NST episode detected in a given day or other period, and thereafter not performed in response to other NST episodes detected during the period, as illustrated with respect to step 318 of FIG. 10. In some examples a period may include a single day, or some other predetermined period. In the example of an NST episode, processing circuitry 106 may store an EGM of the NST episode in memory 108 (YES of 318). Processing circuitry 106 may use the stored EGM to perform the additional LD analysis (320). In response to processing circuity 106 determining that an NST episode does not meet the criteria, or that there is no NST episode (NO of 318), processing circuitry may continue with other tests.

The steps 320, 322 and 324 are similar to the steps 310, 312 and 308 described above, however, steps 320, 322 and 324 may be triggered based on the occurrence of an NST episode, e.g., an average duration of R-R intervals less than a threshold. In contrast, for example, an abnormal periodic performance test in step 308 may trigger processing circuitry 106 to store a near-field or far-field EGM and perform additional LD analysis.

As described above, additional LD analysis may include determining whether the RWA in one or both of the near-field and far-field EGM is low and/or variable (322). In response to processing circuity 106 determining that the RWA is not low or variable (NO of 322), processing circuitry may continue with other tests. In response to processing circuity 106 determining that the RWA is low or variable (YES of 322), processing circuitry 106 may trigger one or more unscheduled performance tests. The performance tests may include a lead impedance measurement, determining whether the RWA had an abrupt decrease and a full pacing threshold test or pacing threshold check as described above. Processing circuitry 106 may analyze the results of the unscheduled performance tests as described above for steps 304 and 308. In other words, after performing an unscheduled performance test (324 of FIG. 10), processing circuitry 106 may detect or not detect ventricular LD based on whether or not one or more of the tests were abnormal.

Steps 326-336 of FIG. 10 may correspond to the functions illustrated and described with respect to FIG. 9. Processing circuitry 106 may employ any technique for detecting ventricular fibrillation (326) as described above in relation to 260 of FIG. 9. Processing circuitry 106 may execute lead dislodgement analysis to confirm VF detection and to avoid inappropriate therapy delivery in response to detecting VF (YES of 326). If processing circuitry 106 does not detect VF, processing circuitry 106 may continue with periodic functions (NO of 326).

As described above in relation to 310 and 320, processing circuitry 106 may analyze both the near-field and far-field stored EGM for R-wave amplitude metrics, including RWA and RWA variability (328). Processing circuitry 106 may further determine whether the RR interval pattern is abnormal in one or both of the EGMs (330). As described above in relation to 266 of FIG. 9, processing circuitry 106 may identify abnormal RR interval patterns based on relatively high RR interval length variability, or an abnormal pattern of RR interval lengths, such as an SLSL pattern (332). In response to determining that RWA and RWA variability does not meet a predetermined threshold, as described above (NO of 332), processing circuitry 106 may confirm VF detection (338). In response to determining that RWA and RWA variability meets the thresholds, described above (YES of 332), processing circuitry 106 may determine whether P-wave amplitudes in one or both of the near-field or far-field EGMs have increased (334) as described above in relation to 314. In response to detecting a P-wave amplitude increase (PWA ↑) (YES of 334), processing circuitry 106 may withhold VF detection (336). In some examples processing circuitry 106 may also trigger a lead dislodgement (LD) alert (316). In response to determining no PWA increase, processing circuitry may confirm VF detection (338). In some examples, processing circuitry 106 may bypass step 334, as described above.

FIG. 11A is a flowchart of another example technique for identifying dislodgment of a ventricular lead including triggering a comparison of stored performance measurements to a predetermined threshold. Where the reference numbers match reference numbers in other figures, the description of the step is the same as described above.

In some examples, processing circuitry 106 of FIG. 2 may perform the steps of FIGS. 11A and 11B during a predetermined time after implant. For example, in response to determining the SIC exceeds a threshold, processing circuity 106 may determine that the time since implant of ventricular lead 20 is less than a threshold amount of time. This is similar to step 300 as described in relation to FIG. 10. Some examples of the threshold amount of amount of time may include three months, six months or thirty days. The threshold amount of time may depend on the type of lead, such as screw-type fixed lead or other type of lead.

In some examples processing circuitry 106 may determine that the SIC exceeds a threshold number of NPSRRI counts (YES of 400). Some examples of a threshold number of NPSRRI counts may include 30 counts in a three-day period, 45 counts in a three-day period, or other similar threshold values. In examples in which SIC does not exceed the threshold number of NPSRRI counts (NO of 400), processing circuitry 106 may continue to conduct other tests (414). Some examples of other tests may include determining the number of NST episodes (318) or VF detection (326) as described above in relation to FIG. 10. The abnormal NPSRRI are different than the abnormal RR interval patterns as described above in relation to step 266 of FIG. 7. In some examples, in response to or otherwise based on determining that the SIC exceeded a threshold, processing circuitry 106 may compare the last stored RWA to an RWA threshold (410). Processing circuitry 106 may additionally or alternatively compare the last stored PT to a PT threshold (410). In response to determining the last stored RWA is less than an RWA threshold (312), and/or the last stored PT is less than a PT threshold (412), processing circuitry 106 may send a lead dislodgement alert (316) as described above in relation to FIG. 1.

Although illustrated in FIG. 11A as requiring both the PT to be greater than a threshold and the RWA to be less than a threshold in order to trigger a lead dislodgement alert, the technique of FIG. 11A may include examples in which the lead dislodgement alert is triggered based on either of the PT being greater than a threshold or the RWA being less than a threshold, as described herein. In some examples, in response to determining that both the SIC exceeded a threshold, and the time since implant is less than a threshold, processing circuitry 106 may trigger detection of a physiological measurement, such as PT or RWA. Following the detection of the physiological measurement, processing circuitry 106 may compare the physiological measurement to a physiological criterion. For example, processing circuitry may measure the RWA and compare the RWA to the RWA threshold.

FIG. 11B is a flowchart of another example technique for identifying dislodgment of a ventricular lead including triggering other performance measurements. Some steps in FIG. 11B are similar to those in FIG. 11A having like numbers. In the example of FIG. 11B, in response to determining that the SIC exceeded a threshold, processing circuitry 106 may trigger a new PT measurement (416). In some examples, processing circuitry may also trigger a new RWA measurement (416).

In some examples, the pacing threshold measurement of this disclosure may be conducted as a pacing threshold check, as described above in relation to step 304 of FIG. 10. A pacing threshold check at a specific voltage may have an advantage over a full pacing threshold analysis in reduced battery capacity consumed, as described above.

Processing circuitry 106 may determine that PT is greater than a predetermined threshold and trigger an NF-EGM and FF-EGM analysis to determine lead dislodgement (418). Steps 310-316 are similar to steps 228 and 310-316 described above in relation to FIGS. 7 and 10. In some examples, processing circuitry 106 may trigger the NF-EGM and FF-EGM analysis only when both the PT is greater than a PT threshold and RWA is less than a predetermined RWA threshold. In other examples, processing circuitry 106 may trigger the NF-EGM and FF-EGM analysis when either the PT is greater than a PT threshold or RWA is less than a predetermined RWA threshold (418).

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. However, the scope of the examples within the techniques of this disclosure is not limited to the described examples. For example, although described in the context of examples, such as FIGS. 7-9, in which one or more EGMs are stored and analyzed in response to a trigger condition, such as a change in impedance, pacing threshold, or R-wave amplitude, an NPSRRI count exceeding a threshold, detection of an NST, or detection of VF, other examples are contemplated. In some examples, the one or more EGMs are stored and/or analyzed prior to detection of such events, e.g., substantially continuously or periodically, and the analysis of one or more R-wave or P-wave metrics as described herein may be triggered by detection of the triggering event. These and other aspects are within the scope of the following examples and the claims.

The following examples illustrate methods, devices, and systems described herein.

Example 1

A method of detecting dislodgement of a ventricular lead coupled to an implantable medical device, the method comprising: sensing, by the implantable medical device, a near-field cardiac electrogram (EGM) via a first electrode of the ventricular lead and a far-field cardiac EGM via a second electrode of the ventricular lead; identifying, by processing circuitry, R-waves in the near-field cardiac EGM and the far-field cardiac EGM; determining, by the processing circuitry: a near-field value of one or more R-wave amplitude metrics based on amplitudes of R-waves identified in the near-field cardiac EGM, and a far-field value of the one or more R-wave amplitude metrics based on amplitudes of R-waves identified in the far-field cardiac EGM; detecting, by the processing circuitry, dislodgement of the ventricular lead based on at least one of the near-field value or the far-field value of the one or more R-wave amplitude metrics; and providing, by the processing circuitry, a lead dislodgment alert in response to detecting the dislodgement of the ventricular lead.

Example 2

The method of example 1, wherein the first electrode comprises a tip electrode of the ventricular lead.

Example 3

The method of example 1 or 2, wherein the second electrode comprises a coil electrode of the ventricular lead.

Example 4

The method of any of examples 1 to 3, wherein the one or more R-wave amplitude metrics comprise an amount of the identified R-waves having an amplitude below an amplitude threshold, and detecting dislodgment of the ventricular lead comprises detecting dislodgement of the ventricular lead based on the amount satisfying a threshold amount.

Example 5

The method of any of examples 1 to 4, wherein the one or more R-wave amplitude metrics comprise a variability of the amplitudes of the identified R-waves and detecting dislodgment of the ventricular lead comprises detecting dislodgement of the ventricular lead based on the variability exceeding a threshold.

Example 6

The method of any of examples 1 to 5, wherein the one or more R-wave amplitude metrics comprise a range of the amplitudes of the identified R-waves and detecting dislodgment of the ventricular lead comprises detecting dislodgement of the ventricular lead based on the range exceeding a threshold.

Example 7

The method of any of examples 1 to 6, further comprising identifying an R-wave amplitude decrease in at least one of the cardiac EGMs, wherein determining the near-field value and the far-field value of the one or more R-wave amplitude metrics comprises determining the near-field value and the far-field value of the one or more R-wave amplitude metrics in response to identifying the R-wave amplitude decrease.

Example 8

The method of any of examples 1 to 7, further comprising identifying a pacing threshold increase in a vector including the first electrode, wherein determining the near-field value and the far-field value of the one or more R-wave amplitude metrics comprises determining the near-field value and the far-field value of the one or more R-wave amplitude metrics in response to detecting the pacing threshold increase.

Example 9

The method of any of examples 1 to 8, further comprising identifying a lead impedance decrease in a vector including the first electrode, wherein determining the near-field value and the far-field value of the one or more R-wave amplitude metrics comprises determining the near-field value and the far-field value of the one or more R-wave amplitude metrics in response to detecting the lead impedance decrease.

Example 10

The method of any of examples 1 to 9, further comprising identifying a P-wave amplitude increase in the at least one of the cardiac EGMs, wherein detecting dislodgement of the ventricular lead comprises detecting dislodgement of the ventricular lead based on the at least one of the near-field value or the far-field value of the one or more R-wave amplitude metrics and the detection of the P-wave amplitude increase.

Example 11

The method of example 10, wherein identifying the P-wave amplitude increase comprises identifying the P-wave amplitude increase in the far-field cardiac EGM.

Example 12

The method of any of examples 1 to 11, further comprising identifying a non-sustained ventricular tachycardia via at least one of the cardiac EGMs, wherein determining the near-field value and the far-field value of the one or more R-wave amplitude metrics comprises determining the near-field value and the far-field value of the one or more R-wave amplitude metrics in response to detecting the non-sustained ventricular tachycardia.

Example 13

The method of example 12, wherein detecting dislodgement of the ventricular lead comprises detecting dislodgement of the ventricular lead based on the at least one of the near-field value or the far-field value of the one or more R-wave amplitude metrics and the identification of the at least one of: an R-wave amplitude decrease in at least one of the cardiac EGMs; a pacing threshold increase in a vector including the first electrode; or a lead impedance decrease in a vector including the first electrode.

Example 14

The method of any of examples 1 to 13, further comprising detecting ventricular fibrillation via at least one of the cardiac EGMs, wherein determining the near-field value and the far-field value of the one or more R-wave amplitude metrics comprises determining the near-field value and the far-field value of the one or more R-wave amplitude metrics in response to detecting the ventricular defibrillation, the method further comprising withholding at least one of the detection of the ventricular fibrillation or delivery of an antitachyarrhythmia shock in response to detecting the dislodgement of the ventricular lead.

Example 15

The method of example 14, further comprising identifying a pattern of RR intervals in at least one of the cardiac EGMs, wherein detecting dislodgement of the ventricular lead comprises detecting dislodgement of the ventricular lead based on the at least one of the near-field value or the far-field value of the one or more R-wave amplitude metrics and the identification of the pattern of RR intervals.

Example 16

The method of example 15, wherein the pattern of RR intervals comprises alternating RR interval lengths.

Example 17

The method of any of examples 14 to 16, further comprising determining a variability of RR intervals of at least one of the cardiac EGMs, wherein detecting dislodgement of the ventricular lead comprises detecting dislodgement of the ventricular lead based on the at least one of the near-field value or the far-field value of the one or more R-wave amplitude metrics and the variability satisfying a variability threshold.

Example 18

The method of any of examples 1 to 17, wherein detecting dislodgement of the ventricular lead comprises detecting dislodgement of the ventricular lead based on both the near-field value and the far-field value of the one or more R-wave amplitude metrics.

Example 19

The method of any of examples 1 to 18, further comprising: determining, by the implantable medical device, a count of RR intervals shorter than an RR interval threshold, wherein the sensing, by the implantable medical device, of the near-field cardiac EGM via the first electrode of the ventricular lead and the far-field cardiac EGM via the second electrode of the ventricular lead is based on the count of RR intervals meeting a threshold number of RR intervals.

Example 20

A medical device system comprising: a ventricular lead comprising a first electrode and a second electrode; an implantable medical device coupled to the ventricular lead and configured to sense a near-field cardiac electrogram (EGM) via the first electrode and a far-field cardiac EGM via the second electrode; and processing circuitry configured to: identify R-waves in the near-field cardiac EGM and the far-field cardiac EGM; determine a near-field value of one or more R-wave amplitude metrics based on amplitudes of R-waves identified in the near-field cardiac EGM and a far-field value of the one or more R-wave amplitude metrics based on amplitudes of R-waves identified in the far-field cardiac EGM; detect dislodgement of the ventricular lead based on at least one of the near-field value or the far-field value of the one or more R-wave amplitude metrics; and provide a lead dislodgment alert in response to detecting the dislodgement of the ventricular lead.

Example 21

The system of example 20, wherein the first electrode comprises a tip electrode of the ventricular lead.

Example 22

The system of example 20 or 21, wherein the second electrode comprises a coil electrode of the ventricular lead.

Example 23

The system of any of examples 20 to 22, wherein the one or more R-wave amplitude metrics comprise an amount of the identified R-waves having an amplitude below an amplitude threshold, and the processing circuitry is configured to detect dislodgment of the ventricular lead based on the amount exceeding a threshold amount.

Example 24

The system of any of examples 20 to 23, wherein the one or more R-wave amplitude metrics comprise a variability of the amplitudes of the identified R-waves and the processing circuitry is configured to detect dislodgment of the ventricular lead based on the variability exceeding a threshold.

Example 25

The system of any of examples 20 to 24, wherein the one or more R-wave amplitude metrics comprise a range of the amplitudes of the identified R-waves and the processing circuitry is configured to detect dislodgment of the ventricular lead based on the range exceeding a threshold.

Example 26

The system of any of examples 20 to 25, wherein the processing circuitry is configured to identify an R-wave amplitude decrease in at least one of the cardiac EGMs, and determine the near-field value and the far-field value of the one or more R-wave amplitude metrics in response to identifying the R-wave amplitude decrease.

Example 27

The system of any of examples 20 to 26, wherein the processing circuitry is configured to identify a pacing threshold increase in a vector including the first electrode, and determine the near-field value and the far-field value of the one or more R-wave amplitude metrics in response to detecting the pacing threshold increase.

Example 28

The system of any of examples 20 to 27, wherein the processing circuitry is configured to identify a lead impedance decrease in a vector including the first electrode, and determine the near-field value and the far-field value of the one or more R-wave amplitude metrics in response to detecting the lead impedance decrease.

Example 29

The system of any of examples 20 to 28, wherein the processing circuitry is configured to identify a P-wave amplitude increase in the at least one of the cardiac EGMs, and detect dislodgement of the ventricular lead based on the at least one of the near-field value or the far-field value of the one or more R-wave amplitude metrics and the detection of the P-wave amplitude increase.

Example 30

The system of example 29, wherein the processing circuitry is configured to identify the P-wave amplitude increase in the far-field cardiac EGM.

Example 31

The system of any of examples 20 to 30, wherein the processing circuitry is configured to identify a non-sustained ventricular tachycardia via at least one of the cardiac EGMs, and determine the near-field value and the far-field value of the one or more R-wave amplitude metrics in response to detecting the non-sustained ventricular tachycardia.

Example 32

The system of example 31, wherein the processing circuitry is configured to detect dislodgement of the ventricular lead based on the at least one of the near-field value or the far-field value of the one or more R-wave amplitude metrics and the identification of the at least one of: an R-wave amplitude decrease in at least one of the cardiac EGMs; a pacing threshold increase in a vector including the first electrode; or a lead impedance decrease in a vector including the first electrode.

Example 33

The system of any of examples 20 to 32, wherein the processing circuitry is configured to detect ventricular fibrillation via at least one of the cardiac EGMs, determine the near-field value and the far-field value of the one or more R-wave amplitude metrics in response to detecting the ventricular defibrillation, and withhold the detection of the ventricular fibrillation in response to detecting the dislodgement of the ventricular lead.

Example 34

The system of example 33, wherein the processing circuitry is configured to identify a pattern of RR intervals in at least one of the cardiac EGMs, and detect dislodgement of the ventricular lead based on the at least one of the near-field value or the far-field value of the one or more R-wave amplitude metrics and the identification of the pattern of RR intervals.

Example 35

The system of example 33, wherein the pattern of RR intervals comprises alternating RR interval lengths.

Example 36

The system of any of examples 32 to 35, wherein the processing circuitry is configured to determine a variability of RR intervals of at least one of the cardiac EGMs, and detect dislodgement of the ventricular lead based on the at least one of the near-field value or the far-field value of the one or more R-wave amplitude metrics and the variability satisfying a variability threshold.

Example 37

The system of any of examples 20 to 36, wherein the processing circuitry is configured to detect dislodgement of the ventricular lead based on the both the near-field value and the far-field value of the one or more R-wave amplitude metrics.

Example 38

The system of any of examples 20 to 37, wherein the processing circuitry comprises processing circuitry of the implantable medical device.

Example 39

The system of any of examples 20 to 38, wherein the processing circuitry is configured to determine a count of RR intervals shorter than an RR interval threshold, and the implantable medical device is configured to: sense the near-field cardiac EGM via the first electrode of the ventricular lead; and sense the far-field cardiac EGM via the second electrode of the ventricular lead, determine lead dislodgement based on the count of RR intervals meeting a threshold number of RR intervals.

Example 40

A method of detecting dislodgement of a ventricular lead coupled to an implantable medical device, the method comprising: sensing, by the implantable medical device, at least one cardiac electrogram (EGM) via the ventricular lead; identifying, by processing circuitry, R-waves and P-waves in the at least one cardiac EGM; determining, by the processing circuitry, a value of one or more R-wave amplitude metrics based on amplitudes of R-waves and a value of one or more P-wave amplitude metrics based on amplitudes of P-wave identified in the EGM; detecting, by the processing circuitry, dislodgement of the ventricular lead based on the values of the one or more R-wave amplitude metrics and the one or more P-wave amplitude metrics; and providing, by the processing circuitry, a lead dislodgment alert in response to detecting the dislodgement of the ventricular lead.

Example 41

The method of example 40, wherein determining the value of the one or more P-wave amplitude metrics comprises determining an amount of P-wave amplitude increase, and detecting dislodgment of the ventricular lead comprises detecting dislodgement of the ventricular lead based on the amount exceeding a threshold.

Example 42

The method of example 40 or 41, wherein determining the value of the one or more P-wave amplitude metrics comprises determining an amount of the identified P-waves having an amplitude above a threshold, and detecting dislodgment of the ventricular lead comprises detecting dislodgement of the ventricular lead based on the amount exceeding a threshold.

Example 43

The method of any of examples 40 to 42, wherein determining the one or more P-wave amplitude metrics comprises determining the one or more P-wave amplitude metrics in response to determining that the value of the one or more R-wave amplitude metrics satisfies a threshold.

Example 44

The method of any of examples 40 to 43, wherein sensing the at least one cardiac EGM via the ventricular lead comprises sensing a near-field cardiac EGM via a first electrode of the ventricular lead and a far-field cardiac EGM via a second electrode of the ventricular lead.

Example 45

The method of example 44, wherein determining a value of one or more R-wave amplitude metrics comprises determining a near-field value of one or more R-wave amplitude metrics based on amplitudes of R-waves identified in the near-field cardiac EGM and a far-field value of the one or more R-wave amplitude metrics based on amplitudes of R-waves identified in the far-field EGM, and detecting dislodgement of the ventricular lead comprises detecting dislodgment of the ventricular lead based on the one or more P-wave amplitude metrics and at least one of the near-field value or the far-field value of the one or more R-wave amplitude metrics.

Example 46

The method of example 45, wherein detecting dislodgement of the ventricular lead comprises detecting dislodgement of the ventricular lead based on the one or more P-wave amplitude metrics and based on both the near-field value and the far-field value of the one or more R-wave amplitude metrics.

Example 47

The method of any of examples 42 to 46, wherein identifying the P-waves comprises identifying the P-waves in the far-field cardiac EGM.

Example 48

The method of any of examples 42 to 47, wherein the first electrode comprises a tip electrode of the ventricular lead.

Example 49

The method of any of examples 42 to 48, wherein the second electrode comprises a coil electrode of the ventricular lead.

Example 50

The method of any of examples 40 to 49, wherein the one or more R-wave amplitude metrics comprise an amount of the identified R-waves having an amplitude below an amplitude threshold, and detecting dislodgment of the ventricular lead comprises detecting dislodgement of the ventricular lead based on the amount exceeding a threshold amount.

Example 51

The method of any of examples 40 to 50, wherein the one or more R-wave amplitude metrics comprise a variability of the amplitudes of the identified R-waves and detecting dislodgment of the ventricular lead comprises detecting dislodgement of the ventricular lead based on the variability exceeding a threshold.

Example 52

The method of any of examples 40 to 51, wherein the one or more R-wave amplitude metrics comprise a range of the amplitudes of the identified R-waves and detecting dislodgment of the ventricular lead comprises detecting dislodgement of the ventricular lead based on the range exceeding a threshold.

Example 53

The method of any of examples 40 to 52, further comprising identifying an R-wave amplitude decrease in the at least one cardiac EGM, wherein determining the one or more R-wave amplitude metrics and the one or more P-wave amplitude metrics comprises determining the one or more R-wave amplitude metrics and the one or more P-wave amplitude metrics in response to identifying the R-wave amplitude decrease.

Example 54

The method of any of examples 40 to 53, further comprising identifying a pacing threshold increase for pacing via the ventricular lead, wherein determining the one or more R-wave amplitude metrics and the one or more P-wave amplitude metrics comprises determining the one or more R-wave amplitude metrics and the one or more P-wave amplitude metrics in response to detecting the pacing threshold increase.

Example 55

The method of any of examples 40 to 54, further comprising identifying a lead impedance decrease of the ventricular lead, wherein determining the one or more R-wave amplitude metrics and the one or more P-wave amplitude metrics comprises determining the one or more R-wave amplitude metrics and the one or more P-wave amplitude metrics in response to detecting the lead impedance decrease.

Example 56

The method of any of examples 40 to 55, further comprising identifying a non-sustained ventricular tachycardia via the at least one cardiac EGM, wherein determining the one or more R-wave amplitude metrics and the one or more P-wave amplitude metrics comprises determining the one or more R-wave amplitude metrics and the one or more P-wave amplitude metrics in response to detecting the non-sustained ventricular tachycardia.

Example 57

The method of example 56, wherein detecting dislodgement of the ventricular lead comprises detecting dislodgement of the ventricular lead based on the one or more R-wave amplitude metrics and the one or more P-wave amplitude metrics and the identification of the at least one of: an R-wave amplitude decrease in the at least one cardiac EGM; a pacing threshold increase for pacing via the ventricular lead; or a lead impedance decrease of the ventricular lead.

Example 58

The method of any of examples 40 to 57, further comprising detecting ventricular fibrillation via the at least one cardiac EGM, wherein determining the one or more R-wave amplitude metrics and the one or more P-wave amplitude metrics comprises determining the one or more R-wave amplitude metrics and the one or more P-wave amplitude metrics in response to detecting the ventricular defibrillation, the method further comprising withholding the detection of the ventricular fibrillation in response to detecting the dislodgement of the ventricular lead.

Example 59

The method any of examples 40 to 58, further comprising identifying a pattern of RR intervals in the at least one cardiac EGM, wherein detecting dislodgement of the ventricular lead comprises detecting dislodgement of the ventricular lead based on the one or more R-wave amplitude metrics and the one or more P-wave amplitude metrics and the identification of the pattern of RR intervals.

Example 60

The method any of examples 40 to 59, wherein the pattern of RR intervals comprises alternating RR interval lengths.

Example 61

The method of any of examples 40 to 60, further comprising determining a variability of RR intervals of the at least one cardiac EGM, wherein detecting dislodgement of the ventricular lead comprises detecting dislodgement of the ventricular lead based on the one or more R-wave amplitude metrics and the one or more P-wave amplitude metrics and the variability satisfying a variability threshold.

Example 62

The method of any of examples 40 to 61, further comprising:
determining, by the implantable medical device, a count of RR intervals shorter than an RR interval threshold, wherein the sensing, by the implantable medical device, at least one cardiac EGM via the ventricular lead is based on the count of RR intervals meeting a threshold number of RR intervals.

Example 63

A medical device system comprising: a ventricular lead; an implantable medical device coupled to the ventricular lead and configured to sense at least one cardiac electrogram (EGM) via the ventricular lead; and processing circuitry configured to: identify R-waves and P-waves in the at least one cardiac EGM; determine a value of one or more R-wave amplitude metrics based on amplitudes of R-waves and a value of one or more P-wave amplitude metrics based on amplitudes of P-wave identified in the EGM; detect dislodgement of the ventricular lead based on the values of the one or more R-wave amplitude metrics and the one or more P-wave amplitude metrics; and provide a lead dislodgment alert in response to detecting the dislodgement of the ventricular lead.

Example 64

The system of example 63, wherein the one or more P-wave amplitude metrics comprises an amount of P-wave amplitude increase, and the processing circuitry is configured to detect dislodgment of the ventricular lead based on the amount exceeding a threshold.

Example 65

The system of example 63 or 64, wherein the one or more P-wave amplitude metrics comprise an amount of the identified P-waves having an amplitude above a threshold, and the processing circuitry is configured to detect dislodgement of the ventricular lead based on the amount exceeding a threshold.

Example 66

The system of any of examples 63 to 65, wherein the processing circuitry is configured to determine the one or more P-wave amplitude metrics in response to determining that the value of the one or more R-wave amplitude metrics satisfies a threshold.

Example 67

The system of any of examples 63 to 66, wherein sensing the at least one cardiac EGM via the ventricular lead comprises sensing a near-field cardiac EGM via a first electrode of the ventricular lead and a far-field cardiac EGM via a second electrode of the ventricular lead.

Example 68

The system of example 67, wherein the processing circuitry is configured to determine a near-field value of one or more R-wave amplitude metrics based on amplitudes of R-waves identified in the near-field cardiac EGM and a far-field value of the one or more R-wave amplitude metrics based on amplitudes of R-waves identified in the far-field EGM, and detect dislodgment of the ventricular lead based on the one or more P-wave amplitude metrics and at least one of the near-field value or the far-field value of the one or more R-wave amplitude metrics.

Example 69

The system of example 68, wherein the processing circuitry is configured to detect dislodgement of the ventricular lead based on the one or more P-wave amplitude metrics and based on both the near-field value and the far-field value of the one or more R-wave amplitude metrics.

Example 70

The system of any of examples 64 to 69, wherein the processing circuitry is configured to identify the P-waves in the far-field cardiac EGM.

Example 71

The system of any of examples 64 to 70, wherein the first electrode comprises a tip electrode of the ventricular lead.

Example 72

The system of any of examples 64 to 71, wherein the second electrode comprises a coil electrode of the ventricular lead.

Example 73

The system of any of examples 63 to 72, wherein the one or more R-wave amplitude metrics comprise an amount of the identified R-waves having an amplitude below an amplitude threshold, and the processing circuitry is configured to detect dislodgement of the ventricular lead based on the amount exceeding a threshold amount.

Example 74

The system of any of examples 63 to 73, wherein the one or more R-wave amplitude metrics comprise a variability of the amplitudes of the identified R-waves and the processing circuitry is configured to detect dislodgement of the ventricular lead based on the variability exceeding a threshold.

Example 75

The system of any of examples 63 to 74, wherein the one or more R-wave amplitude metrics comprise a range of the amplitudes of the identified R-waves and the processing circuitry is configured to detect dislodgement of the ventricular lead based on the range exceeding a threshold.

Example 76

The system of any of examples 63 to 75, wherein the processing circuitry is configured to identify an R-wave amplitude decrease in the at least one cardiac EGM, and determine the one or more R-wave amplitude metrics and the one or more P-wave amplitude metrics in response to identifying the R-wave amplitude decrease.

Example 77

The system of any of examples 63 to 76, wherein the processing circuitry is configured to identify a pacing threshold increase for pacing via the ventricular lead, and determine the one or more R-wave amplitude metrics and the one or more P-wave amplitude metrics in response to detecting the pacing threshold increase.

Example 78

The system of any of examples 63 to 77, wherein the processing circuitry is configured to identify a lead impedance decrease for the ventricular lead, and determine the one or more R-wave amplitude metrics and the one or more P-wave amplitude metrics in response to detecting the lead impedance decrease.

Example 79

The system of any of examples 63 to 78, wherein the processing circuitry is configured to identify a non-sustained ventricular tachycardia via the at least one cardiac EGM, and determine the one or more R-wave amplitude metrics and the one or more P-wave amplitude metrics in response to detecting the non-sustained ventricular tachycardia.

Example 80

The system of example 79, wherein the processing circuitry is configured to detect dislodgement of the ventricular lead based on the one or more R-wave amplitude metrics and the one or more P-wave amplitude metrics and the identification of the at least one of: an R-wave amplitude decrease in the at least one cardiac EGM; a pacing threshold increase for pacing via ventricular lead; or a lead impedance decrease for the ventricular lead.

Example 81

The system of any of examples 63 to 80, wherein the processing circuitry is configured to detect ventricular fibrillation via the at least one cardiac EGM, determine the one or more R-wave amplitude metrics and the one or more P-wave amplitude metrics in response to detecting the ventricular defibrillation, and withhold the detection of the ventricular fibrillation in response to detecting the dislodgement of the ventricular lead.

Example 82

The system of example 81, wherein the processing circuitry is configured to identify a pattern of RR intervals in the at least one cardiac EGM, and detect dislodgement of the ventricular lead based on the one or more R-wave amplitude metrics and the one or more P-wave amplitude metrics and the identification of the pattern of RR intervals.

Example 83

The system of example 82, wherein the pattern of RR intervals comprises alternating RR interval lengths.

Example 84

The system of any of examples 78 to 83, wherein the processing circuitry is configured to determine a variability of RR intervals of the at least one cardiac EGM, and detect dislodgement of the ventricular lead based on the one or more R-wave amplitude metrics and the one or more P-wave amplitude metrics and the variability satisfying a variability threshold.

Example 85

The system of any of examples 63 to 84, wherein the processing circuitry comprises processing circuitry of the implantable medical device.

Example 86

The system of any of examples 63 to 85, wherein the processing circuitry is configured to determine a count of RR intervals shorter than an RR interval threshold, and the implantable medical device is configured to sense at least one cardiac EGM via the ventricular lead based on the count of RR intervals meeting a threshold number of RR intervals.

Example 87

A method of detecting dislodgement of a ventricular lead coupled to an implantable medical device, the method comprising: sensing, by the implantable medical device, a near-field cardiac electrogram (EGM) via the ventricular lead; identifying, by processing circuitry, R-waves in the near-field EGM; determining, by the processing circuitry, a variability of amplitudes of R-waves identified in the near-field EGM; detecting, by the processing circuitry, dislodgement of the ventricular lead based on the variability of the amplitudes of the R-waves; and providing, by the processing circuitry, a lead dislodgment alert in response to detecting the dislodgement of the ventricular lead.

Example 88

The method of example 87, wherein sensing the near-field cardiac EGM comprises sensing the near-field cardiac EGM via a tip electrode of the ventricular lead.

Example 89

The method of example 87 or 88, further comprising: sensing a far-field cardiac EGM via the ventricular lead; and identifying a P-wave amplitude increase in the far-field cardiac EGM, wherein detecting dislodgement of the ventricular lead comprises detecting dislodgement of the ventricular lead based on the variability of the amplitudes of the R-waves and the detection of the P-wave amplitude increase.

Example 90

The method of any of examples 87 to 89, wherein determining the variability of the amplitudes of R-waves comprise determining a range of the amplitudes of the identified R-waves and detecting dislodgment of the ventricular lead comprises detecting dislodgement of the ventricular lead based on the range exceeding a threshold.

Example 91

The method of any of examples 87 to 90, further comprising detecting ventricular fibrillation via the near-field cardiac EGM, wherein determining the variability of the amplitudes of the R-waves comprises determining the variability of the amplitudes of the R-waves in response to detecting the ventricular defibrillation, the method further comprising withholding the detection of the ventricular fibrillation in response to detecting the dislodgement of the ventricular lead.

Example 92

The method of example 91, further comprising identifying a pattern of RR intervals in the near-field cardiac EGM, wherein detecting dislodgement of the ventricular lead comprises detecting dislodgement of the ventricular lead based on the variability of the amplitudes of the R-waves and the identification of the pattern of RR intervals.

Example 93

The method of example 92, wherein the pattern of RR intervals comprises alternating RR interval lengths.

Example 94

The method of any of examples 87 to 93, further comprising determining a variability of RR intervals of the near-field cardiac EGM, wherein detecting dislodgement of the ventricular lead comprises detecting dislodgement of the ventricular lead based on the at least one of the variability of the amplitudes of the R-waves and the variability satisfying a variability threshold.

Example 95

The method of any of examples 87 to 94, further comprising: determining, by the implantable medical device, a count of RR intervals shorter than an RR interval threshold, wherein the sensing, by the implantable medical device, of the near-field cardiac EGM via the ventricular lead is based on the count of RR intervals meeting a threshold number of RR intervals.

Example 96

A medical device system comprising: a ventricular lead; an implantable medical device coupled to the ventricular lead and configured to sense a near-field cardiac electrogram (EGM) via the ventricular lead; and processing circuitry configured to: identify R-waves in the near-field EGM; determine a variability of amplitudes of R-waves identified in the near-field EGM; detect dislodgement of the ventricular lead based on the variability of the amplitudes of the R-waves; and provide a lead dislodgment alert in response to detecting the dislodgement of the ventricular lead.

Example 97

The system of example 96, wherein the implantable medical device senses the near-field cardiac EGM via a tip electrode of the ventricular lead.

Example 98

The system of example 96 or 97, wherein the implantable medical device senses a far-field cardiac EGM via the ventricular lead, and the processing circuitry identifies a P-wave amplitude increase in the far-field cardiac EGM, and detects dislodgement of the ventricular lead based on the variability of the amplitudes of the R-waves and the detection of the P-wave amplitude increase.

Example 99

The system of any of examples 96 to 98, wherein the processing circuitry is configured to determine a range of the amplitudes of the identified R-waves and detect dislodgment of the ventricular lead based on the range exceeding a threshold.

Example 100

The system of any of examples 96 to 99, wherein the processing circuitry is configured to detect ventricular fibrillation via the near-field cardiac EGM, determine the variability of the amplitudes of the R-waves in response to detecting the ventricular defibrillation, and withhold the detection of the ventricular fibrillation in response to detecting the dislodgement of the ventricular lead.

Example 101

The system of example 100, wherein the processing circuitry is configured to identify a pattern of RR intervals in the near-field cardiac EGM, and detect dislodgement of the ventricular lead based on the variability of the amplitudes of the R-waves and the identification of the pattern of RR intervals.

Example 102

The system of example 101, wherein the pattern of RR intervals comprises alternating RR interval lengths.

Example 103

The system of any of examples 96 to 102, wherein the processing circuitry is configured to determine a variability of RR intervals of the near-field cardiac EGM, and detect dislodgement of the ventricular lead based on the at least one of the variability of the amplitudes of the R-waves and the variability satisfying a variability threshold.

Example 104

The system of any of examples 96 to 103, wherein the processing circuitry comprises processing circuitry of the implantable medical device.

Example 105

The system of any of examples 96 to 104, wherein the processing circuitry is configured to determine a count of RR intervals shorter than an RR interval threshold, and the implantable medical device is configured to sense the near field EGM via the ventricular lead based on the count of RR intervals meeting a threshold number of RR intervals.

What is claimed is:
1. A method of detecting dislodgement of a ventricular lead coupled to an implantable medical device, the method comprising:
    sensing, by the implantable medical device, a near-field cardiac electrogram (EGM) via the ventricular lead;
    identifying, by processing circuitry, R-waves in the near-field EGM;

determining, by the processing circuitry, one or more R-wave amplitude variability metrics quantifying a variability of amplitudes of R-waves identified in the near-field EGM;

detecting, by the processing circuitry, dislodgement of the ventricular lead based on the one or more R-wave amplitude variability metrics; and providing, by the processing circuitry, a lead dislodgment alert in response to detecting the dislodgement of the ventricular lead.

2. The method of claim 1, wherein sensing the near-field cardiac EGM comprises sensing the near-field cardiac EGM via a tip electrode of the ventricular lead.

3. The method of claim 1, further comprising:
sensing a far-field cardiac EGM via the ventricular lead; and
identifying a P-wave amplitude increase in the far-field cardiac EGM,
wherein detecting dislodgement of the ventricular lead comprises detecting dislodgement of the ventricular lead based on the one or more R-wave amplitude variability metrics and the detection of the P-wave amplitude increase.

4. The method of claim 1, wherein determining the one or more R-wave amplitude variability metrics comprises determining a range of the amplitudes of the identified R-waves and detecting dislodgment of the ventricular lead comprises detecting dislodgement of the ventricular lead based on the range satisfying a threshold.

5. The method of claim 1, further comprising detecting ventricular fibrillation, wherein determining the one or more R-wave amplitude variability metrics comprises determining the one or more R-wave amplitude variability metrics in response to detecting the ventricular fibrillation, the method further comprising withholding the detection of the ventricular fibrillation or withholding delivery of an antitachyarrhythmia shock in response to detecting the dislodgement of the ventricular lead.

6. The method of claim 1, further comprising identifying a pattern of RR intervals in the near-field cardiac EGM, wherein detecting dislodgement of the ventricular lead comprises detecting dislodgement of the ventricular lead based on the one or more R-wave amplitude variability metrics and the identification of the pattern of RR intervals.

7. The method of claim 6, further comprising detecting ventricular fibrillation, wherein determining the one or more R-wave amplitude variability metrics and identifying the pattern of RR intervals comprises determining the one or more R-wave amplitude variability metrics and identifying the pattern of RR intervals in response to detecting the ventricular fibrillation, the method further comprising withholding the detection of the ventricular fibrillation or withholding delivery of an antitachyarrhythmia shock in response to detecting the dislodgement of the ventricular lead.

8. The method of claim 7, further comprising, by the processing circuitry:
determining an amount of the identified R-waves having an amplitude below an amplitude threshold;
determining a variability of RR intervals of the near-field cardiac EGM;
detecting P-waves in at least one of the near-field cardiac EGM or a far-field cardiac EGM; and
determining at least one of a P-wave amplitude increase based on the detected P-waves or an amount of the detected P-waves having amplitudes satisfying a threshold, wherein detecting dislodgement of the ventricular lead comprises detecting dislodgement of the ventricular lead based on at least one of: the amount of the identified of R-waves having an amplitude below the amplitude threshold, the variability of the RR intervals satisfying the variability threshold, the P-wave amplitude increase, or the amount of the detected P-waves having amplitudes satisfying the threshold.

9. The method of claim 6, wherein the pattern of RR intervals comprises alternating RR interval lengths.

10. The method of claim 1, further comprising determining a variability of RR intervals of the near-field cardiac EGM, wherein detecting dislodgement of the ventricular lead comprises detecting dislodgement of the ventricular lead based on the at least one of the one or more R-wave amplitude variability metrics and the variability of RR intervals satisfying a variability threshold.

11. The method of claim 1, further comprising:
determining, by the processing circuitry, a count of RR intervals shorter than an RR interval threshold,
wherein detecting dislodgment of the ventricular lead comprises detecting dislodgment of the ventricular lead based on the count of RR intervals meeting a threshold number of RR intervals.

12. The method of claim 1, further comprising determining an amount of the identified R-waves having an amplitude below an amplitude threshold, wherein detecting dislodgment of the ventricular lead comprises detecting dislodgement of the ventricular lead based on the amount satisfying a threshold amount.

13. The method of claim 12, further comprising detecting ventricular fibrillation, wherein determining the amount of the identified R-waves having an amplitude below an amplitude threshold comprises determining the amount of the identified R-waves having an amplitude below an amplitude threshold in response to detecting the ventricular fibrillation, the method further comprising withholding the detection of the ventricular fibrillation or withholding delivery of an antitachyarrhythmia shock in response to detecting the dislodgement of the ventricular lead.

14. The method of claim 1, further comprising sensing a far-field cardiac EGM via the ventricular lead.

15. The method of claim 14, wherein sensing the far-field cardiac EGM comprises sensing the far-field cardiac EGM via a coil electrode of the ventricular lead.

16. The method of claim 14, further comprising determining a far-field value of one or more R-wave amplitude metrics based on amplitudes of R-waves identified in the far-field cardiac EGM and detecting, by the processing circuitry, dislodgement of the ventricular lead based on at least one of the one or more R-wave amplitude metrics identified in the far-field cardiac EGM.

17. The method of claim 16, wherein the one or more R-wave amplitude metrics comprise at least one of an amount of the R-waves identified in the far-field cardiac EGM having an amplitude below an amplitude threshold or a variability of the amplitudes of the R-waves identified in the far-field cardiac EGM.

18. The method of claim 14, further comprising:
identifying a P-wave amplitude increase in the far-field cardiac EGM,
wherein detecting dislodgement of the ventricular lead comprises detecting dislodgement of the ventricular lead based on the detection of the P-wave amplitude increase.

19. The method of claim 14, further comprising:
determining an amount of P-waves in the far-field cardiac EGM having an amplitude above a threshold,
wherein detecting dislodgement of the ventricular lead comprises detecting dislodgement of the ventricular lead based on the amount satisfying a threshold.

20. The method of claim 1, further comprising, by the processing circuitry:
detecting at least one of: an R-wave amplitude decrease in at least one of the near-field EGM or a far-field EGM, a pacing threshold increase, a lead impedance decrease, a non-sustained ventricular tachycardia, or a count of RR intervals shorter than an RR interval threshold satisfying a count threshold,
wherein detecting dislodgement of the ventricular lead comprises detecting dislodgement of the ventricular lead based on the detection of the at least one of: an R-wave amplitude decrease in at least one of the near-field EGM or a far-field EGM, a pacing threshold increase, a lead impedance decrease, a non-sustained ventricular tachycardia, or a count of RR intervals shorter than an RR interval threshold satisfying a count threshold.

21. The method of claim 1,
wherein the one or more R-wave amplitude variability metrics comprise one or more of: a quantification of a portion of a group of R-wave amplitudes that are below a threshold amplitude, a range of a group of R-wave amplitudes, or a modesum of a group of R-wave amplitudes, and
wherein detecting dislodgment of the ventricular lead based on the one or more R-wave amplitude variability metrics comprises detecting, by the processing circuitry, dislodgment of the ventricular lead based on at least one of: the quantification exceeding a quantification threshold, the range exceeding a range threshold, or the modesum being less than a modesum threshold.

22. A medical device system comprising:
a ventricular lead;
an implantable medical device coupled to the ventricular lead and configured to sense a near-field cardiac electrogram (EGM) via the ventricular lead; and
processing circuitry configured to:
identify R-waves in the near-field EGM;
determine one or more R-wave amplitude variability metrics quantifying a variability of amplitudes of R-waves identified in the near-field EGM;
detect dislodgement of the ventricular lead based on the one or more R-wave amplitude variability metrics; and
provide a lead dislodgment alert in response to detecting the dislodgement of the ventricular lead.

23. The system of claim 22, wherein the implantable medical device senses the near-field cardiac EGM via a tip electrode of the ventricular lead.

24. The system of claim 22, wherein the implantable medical device senses a far-field cardiac EGM via the ventricular lead, and the processing circuitry is configured to:
identify a P-wave amplitude increase in the far-field cardiac EGM;
detect dislodgement of the ventricular lead based on the detection of the P-wave amplitude increase.

25. The system of claim 22, wherein the processing circuitry is configured to detect ventricular fibrillation, determine the one or more R-wave amplitude variability metrics in response to detecting the ventricular fibrillation, and withhold the detection of the ventricular fibrillation or withhold delivery of an antitachyarrhythmia shock in response to detecting the dislodgement of the ventricular lead.

26. The system of claim 22, wherein the processing circuitry is configured to identify a pattern of RR intervals in the near-field cardiac EGM, and detect dislodgement of the ventricular lead based on the one or more R-wave amplitude variability metrics and the identification of the pattern of RR intervals.

27. The system of claim 26, wherein the processing circuitry is configured to detect ventricular fibrillation, determine the one or more R-wave amplitude variability metrics and identify the pattern of RR intervals in response to detecting the ventricular fibrillation, and withhold the detection of the ventricular fibrillation or withhold delivery of an antitachyarrhythmia shock in response to detecting the dislodgement of the ventricular lead.

28. The system of claim 27, wherein the processing circuitry is configured to:
determine an amount of the identified R-waves having an amplitude below an amplitude threshold;
determine a variability of RR intervals of the near-field cardiac EGM;
detect P-waves in at least one of the near-field cardiac EGM or a far-field cardiac EGM; and
determine at least one of a P-wave amplitude increase based on the detected P-waves or an amount of the detected P-waves having amplitudes satisfying a threshold,
wherein the processing circuitry detects dislodgement of the ventricular lead based on at least one of: the amount of the identified of R-waves having an amplitude below the amplitude threshold, the variability of the RR intervals satisfying the variability threshold, the P-wave amplitude increase, or the amount of the detected P-waves having amplitudes satisfying the threshold.

29. The system of claim 26, wherein the pattern of RR intervals comprises alternating RR interval lengths.

30. The system of claim 22, wherein the processing circuitry is configured to determine a variability of RR intervals of the near-field cardiac EGM, and detect dislodgement of the ventricular lead based on the at least one of the one or more R-wave amplitude variability metrics satisfying an amplitude variability threshold and the variability of the RR intervals satisfying an interval variability threshold.

31. The system of claim 22, wherein one or more R-wave amplitude variability metrics comprise a range of the amplitudes of the identified R-waves and the processing circuitry is configured to detect dislodgment of the ventricular lead based on the range satisfying a threshold.

32. The system of claim 22, wherein the processing circuitry is configured to:
determine a count of RR intervals shorter than an RR interval threshold; and
detect dislodgement of the ventricular lead based on the count of RR intervals meeting a threshold number of RR intervals.

33. The system of claim 22, wherein the implantable medical device is further configured to sense a far-field cardiac EGM via the ventricular lead.

34. The system of claim 33, wherein the processing circuitry is configured to:
   identify R-waves in the far-field cardiac EGM;
   determine a far-field value of one or more R-wave amplitude metrics based on amplitudes of R-waves identified in the far-field cardiac EGM; and
   detect dislodgement of the ventricular lead based on at least one of the far-field values of the one or more R-wave amplitude metrics determined based on R-waves identified in the far-field cardiac EGM.

35. The system of claim 33, wherein one or more R-wave amplitude metrics comprises a variability of amplitudes of R-waves, and wherein the processing circuitry detects dislodgement of the ventricular lead based on a variability of the amplitudes of the R-waves identified in the far-field cardiac EGM.

36. The system of claim 33, wherein the processing circuitry is configured to identify a P-wave amplitude increase in the far-field cardiac EGM, and detect dislodgement of the ventricular lead based on the detection of the P-wave amplitude increase.

37. The system of claim 33, wherein the processing circuitry is configured to:
   determine an amount of P-waves in the far-field cardiac EGM having an amplitude above a threshold, and
   detect dislodgement of the ventricular lead based on the amount satisfying a threshold.

38. The system of claim 22, wherein the processing circuitry is configured to:
   detect at least one of: an R-wave amplitude decrease in at least one of the near-field EGM or a far-field EGM, a pacing threshold increase, a lead impedance decrease, a non-sustained ventricular tachycardia, or a count of RR intervals shorter than an RR interval threshold satisfying a count threshold, and
   detect dislodgement of the ventricular lead based on the detection of the at least one of: an R-wave amplitude decrease in at least one of the near-field EGM or a far-field EGM, a pacing threshold increase, a lead impedance decrease, a non-sustained ventricular tachycardia, or a count of RR intervals shorter than an RR interval threshold satisfying a count threshold.

39. The system of claim 22, wherein the processing circuitry is configured to:
   determine an amount of the identified R-waves having an amplitude below an amplitude threshold; and
   detect dislodgment of the ventricular lead based on the amount exceeding a threshold amount.

40. The system of claim 22, wherein the processing circuitry comprises processing circuitry of the implantable medical device.

41. A medical device system comprising:
   means for sensing a near-field cardiac electrogram (EGM) via the ventricular lead;
   means for identifying R-waves in the near-field EGM;
   means for determining one or more R-wave amplitude variability metrics quantifying a variability of amplitudes of R-waves identified in the near-field EGM;
   means for detecting dislodgement of the ventricular lead based on the one or more R-wave amplitude variability metrics; and
   means for providing a lead dislodgment alert in response to detecting the dislodgement of the ventricular lead.

42. A non-transitory computer-readable storage medium comprising program instructions that, when executed by processing circuitry of a medical device system, cause the processing circuitry to:
   identify R-waves in a near-field cardiac electrogram (EGM) sensed by an implantable medical device via a ventricular lead;
   determine one or more R-wave amplitude variability metrics quantifying a variability of amplitudes of R-waves identified in the near-field EGM;
   detect dislodgement of the ventricular lead based on the one or more R-wave amplitude variability metrics; and
   provide a lead dislodgment alert in response to detecting the dislodgement of the ventricular lead.

* * * * *